US012806387B2

(12) United States Patent
Hooper et al.

(10) Patent No.: US 12,806,387 B2
(45) Date of Patent: Nov. 24, 2026

(54) APPARATUS AND METHODS FOR BIODIFFUSION CHAMBER STORAGE

(71) Applicants: Thomas Jefferson University, Philadelphia, PA (US); IMVAX, Inc., Philadelphia, PA (US)

(72) Inventors: Douglas C. Hooper, Medford, NJ (US); Samantha Garcia, Philadelphia, PA (US); Rhonda Kean, Philadelphia, PA (US); Dominic Ventura, Wilmington, NC (US); Brendan Laurenzi, Rutland, MA (US); David Gregory Honan, Concord, MA (US)

(73) Assignees: Thomas Jefferson University, Philadelphia, PA (US); IMVAX, Inc., Philadelphia, PA (US)

( * ) Notice: Subject to any disclaimer, the term of this patent is extended or adjusted under 35 U.S.C. 154(b) by 1078 days.

(21) Appl. No.: 17/761,123

(22) PCT Filed: Sep. 18, 2020

(86) PCT No.: PCT/US2020/051376

§ 371 (c)(1),
(2) Date: Mar. 16, 2022

(87) PCT Pub. No.: WO2021/055666

PCT Pub. Date: Mar. 25, 2021

(65) Prior Publication Data

US 2022/0370773 A1 Nov. 24, 2022

Related U.S. Application Data

(60) Provisional application No. 62/902,551, filed on Sep. 19, 2019.

(51) Int. Cl.
*A61M 31/00* (2006.01)

(52) U.S. Cl.
CPC ....... *A61M 31/002* (2013.01); *A61M 2205/04* (2013.01)

(58) Field of Classification Search
CPC ........................ A61M 31/002; A61M 2205/04
(Continued)

(56) References Cited

U.S. PATENT DOCUMENTS 3,270,877 A 9/1966 Hecker
3,589,511 A 6/1971 Britt
(Continued)

FOREIGN PATENT DOCUMENTS

CA 2447400 3/2005
CN 103228229 7/2013
(Continued)

OTHER PUBLICATIONS

Schroeteler et al., "Glioma Tissue Obtained by Modern Ultrasonic Aspiration with a Simple Sterile Suction Trap for Primary Cell Culture and Pathological Evaluation," Eur. Surg. Res., 2014;53:37-42.

(Continued)

*Primary Examiner* — Jacob K Ackun
(74) *Attorney, Agent, or Firm* — Riverside Law LLP

(57) ABSTRACT

An apparatus includes a chamber container and a tray. The chamber container has a first portion and a second portion removably coupled to the first portion. The first and second portions collectively define an inner volume. The tray is configured to be removably disposed within the inner volume of the chamber container. The tray includes a first portion and a second portion coupled to the first portion via a hinge. The first portion includes a first retention surface. The second portion includes a second retention surface. The tray is configured to receive a biodiffusion chamber between the first portion and the second portion such that the first
(Continued)

retention surface and the second retention surface engage a portion of the biodiffusion chamber to (1) place the biodiffusion chamber in a predetermined orientation and (2) maintain the biodiffusion chamber in a substantially fixed position relative to the tray.

17 Claims, 11 Drawing Sheets

(58) Field of Classification Search
USPC .................................................. 206/363, 438
See application file for complete search history.

(56) References Cited

U.S. PATENT DOCUMENTS

| | | | | |
|---|---|---|---|---|
| D227,360 | S | 6/1973 | Lou | |
| 3,831,583 | A | 8/1974 | Edmunds | |
| 4,750,619 | A * | 6/1988 | Cohen | B65D 81/127 206/828 |
| 4,816,567 | A | 3/1989 | Cabilly | |
| 4,956,303 | A | 9/1990 | Self | |
| 5,167,638 | A | 12/1992 | Felix | |
| 5,494,162 | A * | 2/1996 | Treace | A61F 2/0095 206/493 |
| 5,583,024 | A | 12/1996 | Mcelroy | |
| 5,621,002 | A | 4/1997 | Bosslet | |
| 5,643,788 | A | 7/1997 | Baserga | |
| 5,674,713 | A | 10/1997 | McElroy | |
| 5,700,670 | A | 12/1997 | Yamagishi | |
| 5,714,170 | A | 2/1998 | Baserga | |
| 5,834,005 | A | 11/1998 | Usala | |
| 6,214,345 | B1 | 4/2001 | Firestone | |
| 6,218,519 | B1 | 4/2001 | Kenten | |
| 6,268,488 | B1 | 7/2001 | Barbas, III | |
| 6,312,684 | B1 | 11/2001 | Baserga | |
| 6,331,526 | B1 | 12/2001 | Baserga | |
| 6,340,674 | B1 | 1/2002 | Baserga | |
| 6,541,036 | B1 | 4/2003 | Andrews | |
| 6,602,677 | B1 | 8/2003 | Wood | |
| 6,677,435 | B2 | 1/2004 | Barbas, III | |
| 6,759,509 | B1 | 7/2004 | King | |
| 6,835,807 | B1 | 12/2004 | Susaki | |
| 7,223,837 | B2 | 5/2007 | De Groot | |
| 7,375,078 | B2 | 5/2008 | Feng | |
| 7,521,541 | B2 | 4/2009 | Eigenbrot | |
| 7,723,485 | B2 | 5/2010 | Junutula | |
| 7,892,222 | B2 | 2/2011 | Vardi | |
| 9,446,168 | B2 | 9/2016 | Barkai | |
| 9,744,187 | B2 | 8/2017 | Nielsen | |
| 10,206,942 | B2 | 2/2019 | Andrews | |
| 10,265,339 | B2 | 4/2019 | Andrews | |
| 10,357,509 | B2 | 7/2019 | Andrews | |
| D868,995 | S | 12/2019 | Tanaka | |
| 10,543,226 | B2 | 1/2020 | Andrews | |
| 10,772,904 | B2 | 9/2020 | Andrews | |
| 11,077,133 | B2 | 8/2021 | Andrews | |
| 11,801,259 | B2 | 10/2023 | Andrews | |
| 12,064,446 | B2 | 8/2024 | Andrews | |
| 2001/0022977 | A1 | 9/2001 | Baserga | |
| 2003/0096743 | A1 | 5/2003 | Senter | |
| 2003/0130189 | A1 | 7/2003 | Senter | |
| 2004/0018194 | A1 | 1/2004 | Francisco | |
| 2004/0052793 | A1 | 3/2004 | Carter | |
| 2004/0098123 | A1 | 5/2004 | Freeman | |
| 2004/0121940 | A1 | 6/2004 | De Groot | |
| 2005/0245906 | A1 | 11/2005 | Makower | |
| 2005/0271615 | A1 | 12/2005 | Shabat | |
| 2006/0100188 | A1 | 5/2006 | Zong | |
| 2006/0116422 | A1 | 6/2006 | De Groot | |
| 2008/0206239 | A1 | 8/2008 | Jones | |
| 2008/0254040 | A1 | 10/2008 | Stefanic | |
| 2009/0005763 | A1 | 1/2009 | Makower | |
| 2009/0202608 | A1 | 8/2009 | Alessi | |
| 2010/0112593 | A1 | 5/2010 | Herman | |
| 2011/0071573 | A1 | 3/2011 | Sixto | |
| 2011/0092572 | A1 | 4/2011 | Tachas | |
| 2011/0217309 | A1 | 9/2011 | Buck | |
| 2012/0272969 | A1 | 11/2012 | Taina | |
| 2014/0346072 | A1 | 11/2014 | Jacobson | |
| 2014/0374414 | A1 | 12/2014 | Lanier | |
| 2015/0000231 | A1 | 1/2015 | Ramirez | |
| 2015/0076023 | A1* | 3/2015 | Kinyon | B65D 51/00 206/438 |
| 2015/0112247 | A1 | 4/2015 | Tempelman | |
| 2015/0152187 | A1 | 6/2015 | Sun | |
| 2015/0320409 | A1 | 11/2015 | Lehmann | |
| 2016/0015454 | A1 | 1/2016 | Goyal | |
| 2016/0157975 | A1* | 6/2016 | Estrada, Jr. | A61C 8/0087 433/173 |
| 2016/0220692 | A1 | 8/2016 | Pienta | |
| 2017/0029514 | A1 | 2/2017 | Kovtun | |
| 2017/0056065 | A1 | 3/2017 | Do | |
| 2017/0056430 | A1 | 3/2017 | Andrews | |
| 2018/0201939 | A1 | 7/2018 | Andrews | |
| 2018/0235996 | A1 | 8/2018 | Andrews | |
| 2018/0256625 | A1 | 9/2018 | Andrews | |
| 2018/0271894 | A1 | 9/2018 | Andrews | |
| 2020/0197149 | A1* | 6/2020 | Folger | A61F 2/0095 |
| 2021/0052875 | A1* | 2/2021 | Laurenzi | A61K 31/7125 |
| 2021/0060055 | A1 | 3/2021 | Andrews | |
| 2021/0403918 | A1 | 12/2021 | Hooper | |
| 2022/0000916 | A1 | 1/2022 | Hooper | |
| 2022/0072025 | A1 | 3/2022 | Andrews | |
| 2022/0195440 | A1 | 6/2022 | Andrews | |
| 2022/0370773 | A1 | 11/2022 | Hooper | |
| 2024/0100078 | A1 | 3/2024 | Andrews | |
| 2025/0009781 | A1 | 1/2025 | Andrews | |

FOREIGN PATENT DOCUMENTS

| | | |
|---|---|---|
| CN | 105142570 | 12/2015 |
| CN | 110832068 | 2/2020 |
| CN | 112795650 | 5/2021 |
| CN | 115605161 | 1/2023 |
| CN | 115697300 | 2/2023 |
| EP | 1900825 | 3/2008 |
| JP | 2001504487 | 4/2001 |
| JP | 2002522506 | 7/2002 |
| JP | 2006524634 | 11/2006 |
| RU | 2611195 | 2/2017 |
| WO | 9614746 | 5/1996 |
| WO | 98013059 | 4/1998 |
| WO | 1998022579 | 5/1998 |
| WO | 2000009145 | 2/2000 |
| WO | 2000009145 A1 | 2/2000 |
| WO | 2000012507 | 3/2000 |
| WO | 2000014746 A1 | 3/2000 |
| WO | 2002088172 | 11/2002 |
| WO | 2003026577 | 4/2003 |
| WO | 2003043583 | 5/2003 |
| WO | 2004032828 | 4/2004 |
| WO | 2004072284 A1 | 8/2004 |
| WO | 2005058367 | 6/2005 |
| WO | 2005079479 | 9/2005 |
| WO | 2005082023 | 9/2005 |
| WO | 2007044515 | 4/2007 |
| WO | 2007085930 | 8/2007 |
| WO | 2009052249 | 4/2009 |
| WO | 2010043880 | 4/2010 |
| WO | 2011130598 | 10/2011 |
| WO | 2011130613 | 10/2011 |
| WO | 2011130615 | 10/2011 |
| WO | 2011130616 | 10/2011 |
| WO | 2015048184 | 4/2015 |
| WO | 2016164916 | 10/2016 |
| WO | 2018165528 | 9/2018 |
| WO | 2018195281 | 10/2018 |

(56) References Cited

FOREIGN PATENT DOCUMENTS

| | | | |
|---|---|---|---|
| WO | 2019147817 | A1 | 8/2019 |
| WO | 2020092684 | | 5/2020 |

OTHER PUBLICATIONS

Shiri et al., 2015, "Dendrosomal Curcumin Suppresses Metastatic Breast Cancer in Mice by Changing M1/M2 Macrophage Balance in the Tumor Microenvironment", Asian Pacific Journal of Cancer Prevention, 16:3917-3922.
Solinas et al., "Tumor-Conditioned Macrophages Secrete Migration-Stimulating Factor: A New Marker for M2-Polarization, Influencing Tumor Cell Motility", J. Immunol., 2010, 185:642-652.
Stein D et al., "The polarity of the dorsoventral axis in the *Drosophila* embryo is defined by an extracellular signal", Cell, 1991, 65:725-735.
Stupp R, Hegi ME, Gorlia T, et al. Cilengitide combined with standard treatment for patients with newly diagnosed glioblastoma with methylated MGMT promoter (Centric EORTC 26071-22072 study): a multicentre, randomised, open-label, phase 3 trial. Lancet Oncol. 2014;15(10):1100-1108.
Stupp R, Hegi ME, Mason WP, et al. Effects of radiotherapy with concomitant and adjuvant temozolomide versus radiotherapy alone on survival in glioblastoma in a randomised phase III study: 5-year analysis of the EORTC-NCIC trial. Lancet Oncol. 2009;10(5):459-466.
Stupp R, Mason WP, van den Bent MJ, et al. Radiotherapy plus concomitant and adjuvant temozolomide for glioblastoma. N Engl J Med. 2005;352(10):987-996.
Sugawara et al., 2002, "Nestin as a Marker for Proliferative Endothelium in Gliomas" Laboratory Investigation, 82:345-351.
Sun et al. "Blockage of IGF-1R signaling sensitizes urinary bladder cancer cells to mitomycin-mediated cytotoxicity," Cell Research. Jun. 1, 2001 (Jun. 1, 2001). vol. 11, No. 2, pp. 107-115.
Syn et al., 2017, "Exosomes In Cancer Nanomedicine and Immunotherapy: Prospects and Challenges", Trends in Biotechnology, 35:665-676.
Verbrugge I et al., "Radiotherapy Increases the Permissiveness of Established Mammary Tumors to Rejection by Immunomodulatory Antibodies", Cancer Res., 2012, 72:3163-3174.
Vogel et al., 1995, "A Compendium of Vaccine Adjuvants and Excipients (2nd Edition)", Pharm. Biotechnol., 6:141-228.
Weigel, B, Controlling Operating Room Temperature and Humity, and Managing Expectations, (Dec. 17, 2015), URL: https://buildingenergy.cx-associates.com/2014/12/controlling-operating-room-temperature-and-humidity-and-managing-expectations, (May 1, 2018), XP055542468.
Wen PY, Chang SM, Van den Bent MJ, Vogelbaum MA, Macdonald DR, Lee EQ. Response Assessment in Neuro-Oncology Clinical Trials. J Clin Oncol. 2017;35(21):2439-2449.
Zhou Liangfu, "Modern Neurosurgery", p. 605, Fudan University Press, date of publication: Jan. 31, 2015.
Zhou W. et al., "Periostin Secreted by Glioblastoma Stem Cells Recruits M2 Tumor-associated Macrophasges and Promotes Malignant Growth", Nat. Cell. Biol., 2015, 17:170-182.
Chinese Office Action (including English translation) issued in App. No. CN2019800165927, dated Mar. 7, 2024, 23 pages.
Office Action (Notice of Allowance and Fees Due (PTOL-85)) dated Jun. 18, 2024 for U.S. Appl. No. 17/365,209 (pp. 1-3).
Xu Liang et al., Are antisense, RNA interference, and gene silencing strategies feasible for disease treatment? (Jul. 10, 2009), International Journal of Pharmaceutical Research, No. 03, pp. 223-226. DOI: 10.3969/j.issn.1674-0440.2009.03.013.
"Antisense 102: Pilot Immunotherapy for Newly Diagnosed Malignant Glioma." ClinicalTrials.gov, NCT02507583, First Received Jun. 29, 2015, Verified Apr. 2016 by Thomas Jefferson University, 4 pages.
"Pilot Immunotherapy Trial for Recurrent Malignant Gliomas." ClinicalTrials.gov, NCT01550523, Study Completed, First Received Feb. 14, 2012, Verified Dec. 2013 by Thomas Jefferson University, 4 pages.
Andrews DW et al., "Phase 1 Trial of Vaccination with Autologous Tumor Cells and Antisense Directed Against the Insulin Growth Factor Type 1 Receptor (IGF-1 R AS ODN) in Patients with Recurrent Malignant Glioma." Departments of Neurological Surgery, Thomas Jefferson University, Philadelphia, PA, Feb. 12, 2016, 10 pages.
Andrews DW et al., "Results of a Pilot Study Involving the Use of an Antisense Oligodeoxynucleotide Directed Against the Insulin-Like Growth Factor Type I Receptor in Malignant Astrocytomas." Journal of Clinical Oncology, 2001, 19: 2189-2200.
Andrews et al., 2021, "Phase 1b Clinical Trial of IGV-001 for Patients with Newly Diagnosed Glioblastoma", Clinical Cancer Research, vol. 27, No. 7, pp. 1912-1922.
Andrews, D.W., et al., "Phase 1 Trial of Vaccination with Autologous Tumor Cells and Antisense Directed Against the Insulin Growth Factor Type 1 Receptor (IGF-1 R AS ODN) in Patients with Recurrent Malignant Glioma," JHN Journal, Winter 2018, vol. 13, Issue 1, Article 2, pp. 7-13.
Baserga R et al., "The role of the IGF-I receptor in apoptosis", Vitamins & Hormones, 1997, 53:65-98.
Bohula et al, 2003, "Targeting the type insulin like growth factor receptor as anti-cancer treatment" Anticancer Drugs, 14:669-682.
Chinese Journal of Hepatobiliary Surgery, 2007, vol. 13, No. 4, pp. 261-264.
Chinese Office Action (including English translation) issued in App. No. CN20188018150, dated Jul. 20, 2023, 17 pages.
Chinot OL, Wick W, Mason W, et al. Bevacizumab plus radiotherapy-temozolomide for newly diagnosed glioblastoma. N Engl J Med. 2014;370(8):709-722.
Day et al., "Glioma surgical aspirate: A viable source of tumor tissue for experimental research," Cancers, 2013, 5:357-371.
De Vries M et al., "Tumor-Associated Macrophages Are Related to Volumetric Growth of Vestibular Schwannomas", Otology & Neurotology, 2013, 34:347-352.
Dlouhy et al., "Emerging technology in intracranial neuroendoscopy: application of the NICO Myriad," Neurosurgical Focus, Apr. 2011; 30(4):E6, 9 pages. doi: 10.3171/2011.2.FOCUS10312.
Durfort et al., 2012, "Small Interfering RNA Targeted to IGF-IR Delays Tumor Growth and Induces Proinflammatory Cytokines in a Mouse Breast Cancer Model", PLOS ONE, 12 pages, 7:e29213.
Emoto K. et al., "Mechanisms of Heat-Induced Antigen Retrieval: Does PH or Ionic Strength of the Solution Play a Role for Refolding Antigens?", Journal of Histochemistry and Cytochemistry, 2005, 53:1311-1321.
Fang et al., 2016, "Targeted gene silencing of CCL2 inhibits triple negative breast cancer progression by blocking cancer stem cell renewal and M2 macrophage recruitment", Oncotarget, 7:49349-49367.
Farabaugh et al., 2015, "Role of IGF1R in breast cancer subtypes, stemness, and lineage differentiation" Front Endocrinol (Lausanne). 6:59;1-12.
Garcia Samantha et al., Treatment of glioma cells with IGF-IR antisense and irradiation induces the T production of antigens that stimulate IFN[gamma] production by tumor-specific CD4 T cells, Cancer Immunology Research, vol. 8, No. 4_Supplement, Apr. 1, 2020 (Apr. 1, 2020), pp. B86-B86.
Gilbert MR, Dignam JJ, Armstrong TS, et al. A randomized trial of bevacizumab for newly diagnosed glioblastoma. N Engl J Med. 2014;370(8):699-708.
Gilbert MR, Wang M, Aldape KD, et al. Dose-dense temozolomide for newly diagnosed glioblastoma: a randomized phase III clinical trial. J Clin Oncol. 2013;31(32):4085-4091.
Green LC et al., "Analysis of Nitrate, Nitrite, and [15N]Nitrate in Biological Fluids", Analytical Chemistry, 1982, 126:131-138.
Harshyne LA et al., "Th2 bias in glioblastoma patient peripheral blood", Neuro-Oncology, 2016, 18:206-215.

(56) References Cited

OTHER PUBLICATIONS

Harshyne LA et al., "Glioblastoma exosomes and IGF-1 RIAS-ODN are immunogenic stimuli in a translational research immunotherapy paradigm." Cancer Immunother., 2015, 64:299-309.
Hegi ME, Diserens AC, Gorlia T, et al. MGMT gene silencing and benefit from temozolomide in glioblastoma. N Engl J Med. 2005;352(10):997-1003.
Huang et al., 2017, "Curcumol triggers apoptosis of p53 mutant triple-negative human breast cancer MDA-MB 231 cells via activation of p73 and PUMA", Oncol. Lett., 14:1080-1088.
Iaccarino et al. 2015, "Proognostic value of MGMT promoter status in non-resectable glioblastoma after adjuvant therapy", Clinical Neurology and Neurosurgery, 132:1-8.
Jin et al., "Cell surface Nestin is a biomarker for glioma stem cells," Biochem Biophys Res Commun., 2013, 433:496-501.
Kanno H et al., "Expression of CD163 prevents apoptosis through the production of granulocyte colonystimulating factor in meningioma", Neuro-Oncology, 2013, 15:853-864.
Kong DS, Nam DH, Kang SH, et al. Phase III randomized trial of autologous cytokine-induced killer cell immunotherapy for newly diagnosed glioblastoma in Korea. Oncotarget. 2017;8(4):7003-7013.
Lange AM et al., "IL-4- and IL-5-dependent Protective Immunity to Onchocerca Volvulus Infective Larvae in BALB/cBYJ Mice", J. Immunology, 1994, 153:205-211.
Lange, et al., 1994, "IL-4- and IL-5-dependent protective immunity to Onchocerca volvulus infective larvae in BALB/cBYJ mice", J. Immunol., 153:205-211.
Lanza RP et al., "Xenogenic Humoral Responses to Islets Transplanted in Biohybrid Diffusion Chambers", 1994, Transplantation, 57:1371-1375.
Liu et al., "Clinical implications for nestin protein expression in breast cancer". Cancer Sci. Dec. 17, 2009; 101: 815-819 (Year: 2009).
Lumnickzky et al., 2002, "Local tumor irradiation augments the antitumor effect of cytokine-producing autologous cancer cell vaccines in a murine glioma model", Cancer Gene Therapy, 9:44-52.
Mao Ying, Mao Ying's Viewpoint on Glioma in 2016, p. 204, Scientific and Technical Documentation Press.
Martinez et al., "Transcriptional Profiling of the Humanl Monocyte-to-Macrophage Differentiation and Polarization: New Molecules and Patterns of Gene Expression," J Immunol., 2006, 177:7303-7311.
McLaughlin N., et al., "Side-Cutting Aspiration Device for Endoscopic and U Microscopic Tumor Removal", Journal of Neurological Surgery Part B, Skull Base, 2012, 73:11-20.
Morin-Brureau M et al., "Enhancement of glioma-specific immunity in mice by "NOBEL", an insulin-like growth factor 1 receptor antisense oligodeoxynucleotide", Cancer Immunother., 2015, 64:447-457.
National Cancer Institute. IGF-1 R antisense oligodeoxynucleotide-treated autologous glioma cells [online], Jul. 24, 2018, 5 pages.
National Comprehensive Cancer Network. NCCN Clinical Practice Guidelines in Oncology: Central Nervous System Cancers, 34 pages. 2020. https://www.nccn.org/professionals/physician_gls/pdf/cns.pdf.
Okada H, Weller M, Huang R, et al. Immunotherapy response assessment in neuro-oncology: a report of the RANO working group. Lancet Oncol. 2015;16(15):e534-e542.
Okwan-Duodu et al., "Obesity-driven inflammation and cancer risk: role of myeloid derived suppressor cells and altenmtely activated macrophages," Am. J. Cancer Res., 2013, 3:21-33.
Pian et al., 2018, "Targeting the IGFIR Pathway in Breast Cancer Using Antisense IncRNA-Mediated Promoter cis Competition" Molecular Therapy Nucleic Acids, 105-117.
Prosniak M et al., "Glioma Grade Is Associated with the Accumulation and Activity of Cells Bearing M2 Monocyte Markers", Clinical Cancer Research, 2013, 19:3776-3786.
Ramcharan et al. 2015, "IGF-1 R inhibition induces schedule-dependent sensitization of human 1-12 melanoma to temozolomide," Oncotarget, vol. 6, Iss. 37, 39877-39890.
Resnicoff et al., 1994, "Growth inhibition of human melanoma cells in nude mice by antisense strategies to the type 1 insulin-like growth factor receptor", Cancer Research, 54:4848-4850.
Resnicoff M., et al., "The Insulin-like Growth Factor I Receptor Protects Tumor Cells from Apoptosis in Vivo", American Association for Cancer Research, 1995, 55:2463-2469.
Rushing et al., "High-grade astrocytomas show increased nestin and Wilms's tumor gene (WT1) protein expression", International Journal of Surgical Pathology, 2010, 18:255-259.
Schillaci, R., et al., "Immunization with Murine Breast Cancer Cells Treated with Antisense Oligodeoxynucleotides to Type I Insulin-Like Growth Factor Receptor Induced an Antitumoral Effect Mediated by a CD8+ Response Involving Fas/Fas Ligand Cytotoxic Pathway." The Journal of Immunology (2006); 176: 3426-3437.
Han et al., 2017, "STAT3-blocked whole-cell hepatoma vaccine induces cellular and humoral immune response against HCC", J. Exper. & Clin. Cancer Res, 36:156, 11 pages.
Johnstone et al., 2015, "Functional and molecular characterisation of EO771.LMB tumours, a new C57BL/6-mouse- derived model of spontaneously metastatic mammary cancer", Disease Models and Mechanisms, 8:237-251.
Kiliniakis et al., 2009, "Igf1r as a therapeutic target in a mouse model of basal-like breast cancer", Proceedings of the National Academy of Sciences, 106:2359-2364.
Pingili et al., 2021, "Immune checkpoint blockade reprograms systemic immune landscape and tumor microenvironment in obesity-associated breast cancer", Cell Reports, 35:109285, 21 pages.
Zhang et al., 2006, "Effect of blocking IGF-I receptor on growth of human hepatocellular carcinoma cells", World J Gastroenterology, 12:3977, 6 pages.
Arai et al., 2012, "Nestin expression in brain tumors: its utility for pathological diagnosis and correlation with the prognosis of high-grade gliomas," Brain Tumor Pathol, 29, p. 160-167 (Year: 2012).
NIH Clinical Trials, "Pilot Immunotherapy Trial for Recurrent Malignant Gliomas," ID: NCT01550523, Record submitted Dec. 2, 2013, accessed Aug. 18, 2025 (Year: 2013).
Office Action (Final Rejection) dated Sep. 16, 2025 for U.S. Appl. No. 17/290,797 (pp. 1-24).
Office Action (Non-Final Rejection) dated Aug. 26, 2025 for U.S. Appl. No. 17/599,023 (pp. 1-53).
Pearson and Regad, Sep. 29, 2017, Signal Transduction and Targeted Therapy, 2, e17040, p. 1-11 (Year: 2017).

* cited by examiner

APPARATUS AND METHODS FOR BIODIFFUSION CHAMBER STORAGE

CROSS-REFERENCE TO RELATED APPLICATIONS

This application a national phase application under 35 U.S.C. § 371 claiming benefit to PCT International Application PCT/US2020/051376, filed Sep. 18, 2020, which claims priority under 35 U.S.C. § 119 (e) to and the benefit of U.S. Provisional Application No. 62/902,551, filed Sep. 19, 2019, the disclosures of which are incorporated herein by reference in their entireties.

FIELD OF THE DISCLOSURE

The present disclosure relates to the fields of medical devices and/or medicine. More particularly, the disclosure relates to storage devices for at least temporarily storing one or more biodiffusion chambers.

BACKGROUND

Implantable biodiffusion chambers are used for various applications including systemic and local drug delivery, gene therapy, and autologous cell vaccination. Biodiffusion chambers may be implanted into a subject during surgery, and removed after a therapeutically effective amount of time. In some implementations, biodiffusion chambers can be loaded with a composition (e.g., a composition including at least a mixture of cells and antisense molecules) during the surgical procedure in which the chambers are inserted into the subject. It is therefore, desirable to limit and/or reduce loading times to prevent delays and/or potential adverse outcomes associated with prolonged surgical procedures.

Some known biodiffusion chambers can be relatively small chambers, which can be difficult to handle, manipulate, load, and/or insert into or remove from the body of a subject. For example, some known ways of manipulating biodiffusion chambers can include grasping a chamber around or about its full diameter with forceps, which can result in a risk of slipping and/or puncturing a portion of the chamber. Moreover, in some known instances, the loading of drugs, therapies, and/or compositions into the biodiffusion chambers can be cumbersome and/or time consuming. Accordingly, there remains a need for improved storage of biodiffusion chambers that can facilitate, inter alia, the handling and/or loading of the chambers.

SUMMARY

In some embodiments, an apparatus configured to at least temporarily store one or more biodiffusion chambers includes a chamber container and a tray. The chamber container has a first portion and a second portion configured to be removably coupled to the first portion. The first portion and the second portion of the chamber container collectively define an inner volume. The tray is configured to be removably disposed within the inner volume of the chamber container. The tray includes a first portion and a second portion coupled to the first portion via a hinge. The first portion includes a first retention surface. The second portion includes a second retention surface. The tray is configured to receive a biodiffusion chamber between the first portion and the second portion such that the first retention surface and the second retention surface engage a portion of the biodiffusion chamber to (1) place the biodiffusion chamber in a predetermined orientation and (2) maintain the biodiffusion chamber in a substantially fixed position relative to the tray.

BRIEF DESCRIPTION OF THE DRAWINGS

The following drawings form part of the present specification and are included to further demonstrate certain aspects of the present disclosure. The disclosure may be better understood by reference to these drawings in combination with the detailed description of specific embodiments presented herein.

DETAILED DESCRIPTION

Figure 1:
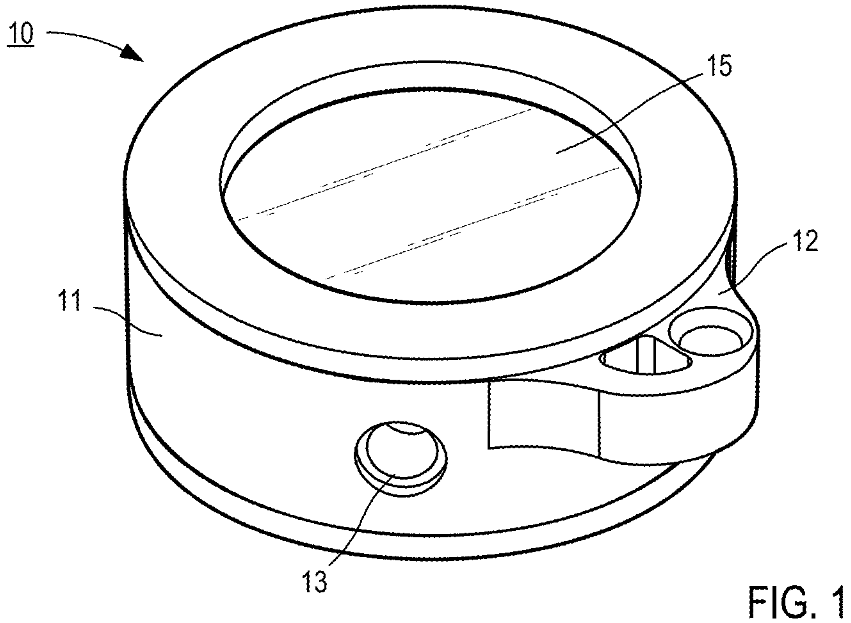
FIG. 1 is a perspective view of a biodiffusion chamber according to an embodiment.

In some embodiments, an apparatus configured to at least temporarily store one or more biodiffusion chambers includes a chamber container and a tray. The chamber container has a first portion and a second portion configured to be removably coupled to the first portion. The first portion and the second portion of the chamber container collectively define an inner volume. The tray is configured to be removably disposed within the inner volume of the chamber container. The tray includes a first portion and a second portion coupled to the first portion via a hinge. The first portion includes a first retention surface. The second portion includes a second retention surface. The tray is configured to receive a biodiffusion chamber between the first portion and the second portion such that the first retention surface and the second retention surface engage a portion of the biodiffusion chamber to (1) place the biodiffusion chamber in a predetermined orientation and (2) maintain the biodiffusion chamber in a substantially fixed position relative to the tray.

In some embodiments, the chamber container can be configured to receive a set of trays arranged in a stacked configuration. For example, a first tray can at least temporarily store a first set of biodiffusion chambers between a first portion and a second portion of the first tray. Similarly, a second tray can at least temporarily store a second set of biodiffusion chambers between a first portion and a second portion of the second tray. A contour of, for example, a chamber region of each of the first tray and the second tray can allow the biodiffusion chambers to be disposed within the trays. In addition, the chamber regions are such that a contour of the second portion of the second tray is similar to and/or at least partially corresponds to a contour to the first portion of the first tray, thereby allowing the first tray and the second tray to be stacked.

In some embodiments, the apparatus configured to at least temporarily store the one or more biodiffusion chambers can also be configured to store one or more tools used in conjunction with the biodiffusion chambers. For example, the chamber container can be coupled to one or more tool containers configured to at least temporarily store the one or more tools. In some embodiments, the tool containers can be configured to couple to the chamber container in a stacked configuration. In some embodiments, the tool containers can include a separate tool for each biodiffusion chamber included in the chamber container. The tools can be disposable or reusable. In some instances, the tools can be used to insert a plug into a hole or port used to load the biodiffusion chambers with a substance, drug, composition, etc.

In some embodiments, a biodiffusion chamber configured for insertion into and removal from a body includes (i) a chamber body defining a hollow cavity; (ii) a first semi-permeable membrane coupled to a first surface of the chamber body; (iii) a second semi-permeable membrane coupled to a second surface of the chamber body; and (iv) an element and/or feature adapted for removing and/or facilitating a process of removing the biodiffusion chamber from the human body. In some embodiments, the biodiffusion chamber can be disposed in a tray or other storage system prior to being inserted into the body. In some such embodiments, the tray can include any number of surfaces that can selectively engage the biodiffusion chamber to at least temporarily maintain the biodiffusion chamber in a fixed position relative to the tray or storage system. For example, the surface(s) can engage and/or can be in contact with the element and/or feature of the biodiffusion chamber to at least temporarily maintain the biodiffusion chamber in a substantially fixed position relative to the tray. As described in detail herein, in some instances, the biodiffusion chamber can be at least temporarily maintained in an orientation that enables and/or facilitates loading the hollow cavity of the biodiffusion chamber with a drug, composition, and/or the like. The biodiffusion chambers described herein may be used for various applications including but not limited to systemic and local drug delivery, gene therapy, autologous cell vaccination, and/or the like.

Other objects, features, and/or advantages of the present disclosure will become apparent from the following detailed description. It should be understood, however, that the detailed description and the specific examples, while indicating specific embodiments of the disclosure, are given by way of illustration only. Various changes and/or modifications within the spirit and scope of the disclosure will become apparent to those skilled in the art from this detailed description.

As used in this specification, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

All of the ranges listed herein are intended to include the endpoint values. For example, a range of whole numbers between 5 and 10 includes the values 5, 6, 7, 8, 9, and 10. The terms "about" and "approximately" can be used interchangeably herein and generally refer to a range of plus or minus 10% of the indicated value. For example, about 0.5 would include 0.45 and 0.55, about 10 would include 9 to 11, about 1000 would include 900 to 1100, etc.

The term "substantially" when used in connection with a geometric construction and/or geometric relationship is intended to convey that the structure so defined is nominally the geometric construction and/or geometric relationship. As one example, a portion of a chamber body that is described as being "substantially annular" is intended to convey that, although an annular (e.g., ring-shape) of the portion is desirable, some variance can occur in a "substantially annular" portion. Such variances can result from manufacturing tolerances or other practical considerations (e.g., a pressure or a force applied to a surface, and/or the like). Thus, a geometric construction modified by the term "substantially" is intended to refer to such a geometric construction within a tolerance, for example, of plus or minus 10% of the stated geometric construction.

Embodiments, devices, and/or components described herein may include, comprise, consist of, and/or be formed from any biocompatible material(s), such as one or more biocompatible polymers. The biocompatible polymer(s) may be a linear polymer, a branched polymer, a cross-linked polymer, a network polymer, and/or the like. For example, the biocompatible polymer(s) may include, comprise, and/or consist of poly(lactides), poly(glycolides), poly(lactide-co-glycolides), poly(lactic acid)s, poly(glycolic acid)s, polycarbonates, polyesteramides, polyanhydrides, polyorthoesters, poly(dioxanone)s, polycaprolactones, polyurethanes, polycyanoacrylates, and blends thereof and copolymers thereof. Examples of biocompatible polymers may include poly-(lactide-co-glycolide) (PLGA), poloxamer, polyvinylpyrrolidone (povidone or PVP), PVP ethylcellulose, sodium pyrrolidone carboxylate, poly(ethylene glycol) (PEG), poly(vinyl alcohol) (PVA), poly-(D,L-lactide-co-glycolide), poly(N-isopropyl acrylamide) (PIPA), poly(lactic acid) (PLLA or PLA), PEG-PLA, polyvinylchloride (PVC), polytetrafluroethylene (PTFE), polyethersulfone (PES), polyethylene (PE), polyetheretherketone (PEEK), polysulfone (PS), polypropylene (PP), poly(methyl methacrylate) (PMMA), poly(N-isopropyl acrylamide) (NIPAAM), gelatin, collagen, starch, or blends thereof or copolymers thereof. For example, some biodiffusion chambers described herein can comprise and/or can be formed at least in part from substantially pure PMMA or suitable blends of PMMA. In other embodiments, a biodiffusion chamber can comprise and/or can be formed from a polycarbonate and/or a substantially pure polycarbonate. Moreover, the storage systems, devices, and/or components thereof may include, comprise, consist of, and/or be formed from any of the biocompatible material(s) described above. In other embodiments, the storage systems, devices, and/or components thereof may be formed of any other suitable material including, for example, materials that may have limited biocompatibility.

Biodiffusion Chamber

FIG. 1 depicts a biodiffusion chamber 10, according to an embodiment. As shown, the biodiffusion chamber 10 includes and/or comprises a chamber body 11, and a pair of semi-permeable membranes 15 disposed on or coupled to opposite sides of the chamber body 11. The biodiffusion chamber 10 is configured to at least temporarily contain a composition including at least a biologic factor (e.g., a composition including a mixture of cells, antisense molecules, a buffer, and/or any other additional agents such as small molecule drugs, additional and/or different antisense molecule(s), additional and/or different buffer(s), and/or the like). Moreover, the biodiffusion chamber 10 is configured to be inserted into a subject (e.g., an animal, mammal, human, and/or mouse) and removed from the subject after a predetermined time (e.g., a therapeutically effective time of about 3 hours to about 72 hours, as described above).

In some embodiments, the biodiffusion chamber 10 can be similar to and/or substantially the same as any of the biodiffusion chambers described in WIPO Publication No. WO 2019/147817, filed Jan. 24, 2019 and entitled, "Biodiffusion Chamber" (referred to herein as the "'961 publication") the disclosure of which is incorporated herein by reference in its entirety. Accordingly, while certain components, elements, and/or features of the biodiffusion chamber 10 are identified and briefly discussed below, the biodiffusion chamber 10 is not described in further detail herein and should be considered similar to the biodiffusion chambers described in the '961 publication unless the explicitly stated otherwise.

The chamber body 11 includes a flange 12 and defines an injection port 13. The chamber body 11 may have any shape, size, and/or configuration such as those described in the '961 publication. For example, as shown in FIG. 1, the chamber body 11 can have a substantially cylindrical outer shape and can be annular or ring-shaped, with the exception of a flange 12 extending out from the chamber body 11—or a surface or side of the chamber body 11—to facilitate handling of the biodiffusion chamber 10 and/or insertion or removal of the biodiffusion chamber 10 from a subject (e.g., from the human body).

The chamber body 11 has a first side or surface and a second side or surface that is opposite the first side or surface. Each of the first and second side or surface is coupled to one of the pair of semi-permeable membranes 15, as described in further detail herein. The chamber body 11 is substantially annular with a set of walls that define a hollow cavity within the chamber body 11. In some embodiments, the walls of the chamber body 11 between an exterior surface and an interior surface are about 2.0 mm thick. In some embodiments, the arrangement and/or configuration of the chamber body 11 can be such that a height or distance between the first side and the second side is about 4.5 mm, a diameter of the hollow cavity is about 10.0 mm, and a volume of the hollow cavity is about 350.0 μL. In other embodiments, the chamber body 11 can have any suitable shape, size, and/or configuration such as any of those described in the '961 publication.

The flange 12 of the chamber body 11 can be any suitable shape, size, and/or configuration. In some embodiments, the flange 12 has a height less than the height of the chamber body 11 (e.g., less than about 4.5 mm). The flange 12 can include, form, and/or define any suitable feature, element, opening, hole, and/or the like. As described in further detail herein, in some embodiments, the biodiffusion chamber 10 can be positioned within a portion of a storage tray and/or other storage device such that a portion of the tray and/or device selectively engages, for example, the flange 12 to maintain the biodiffusion chamber 10 in a substantially fixed position and/or orientation relative to the tray and/or device.

The injection port 13 of the chamber body 11 can be any suitable shape, size, and/or configuration. The injection port 13 extends through a wall of the chamber body 11 from an exterior surface of the chamber body 11 to an interior surface of the chamber body 11. In some embodiments, the diameter of the injection port 13 is based on a size of a pipette or pipette tip used to convey fluid and/or a composition including at least one or more biologic factors into the hollow cavity of the chamber body 11. In other embodiments, the diameter of the injection port 13 can be substantially the same as the injection port diameters described in the '961 publication. Moreover, the fluid and/or composition conveyed into the hollow cavity via the injection port 13 can be any of the fluids and/or compositions described in the '961 publication.

In some embodiments, the injection port 13 is sealed or at least temporarily sealed after injection of a fluid or a composition including at least a biologic factor into the hollow cavity. The injection port 13 can be reversibly or irreversibly sealed. In some embodiments, the injection port 13 can be sealed by inserting a seal member, stopper, plunger, plug, and/or the like into the injection port 13 (collectively referred to as a "plug"). The plug can be any suitable shape size, and/or configuration and can be formed from any suitable material. For example, in some embodiments, the plug can be substantially similar in at least form and/or function to the plugs, seal members, etc. described in the '961 publication. As described in further detail herein, in some embodiments, the biodiffusion chamber 10 can be positioned within a portion of a storage tray and/or other storage device such that the injection port 13 is maintained in a substantially fixed and accessible position and/or orientation relative to the tray and/or device, which can allow a fluid or composition to be conveyed into the hollow chamber via the injection port 13 and the injection port 13 to be sealed after the conveyance. Moreover, in some implementations, the storage system 100 can store one or more tools, which can be used to seal the injection port 13 after the conveyance.

The biodiffusion chamber 10 includes the pair of semi-permeable membranes 15, with a first semi-permeable membrane 15 coupled to the first side of the chamber body 11 and a second semi-permeable membrane 15 coupled to the second side of the chamber body 11. The semi-permeable membranes can be directly coupled to the chamber body 11 or can be coupled via a retention member coupled to each side of the chamber body 11. In some embodiments, the hollow cavity of the chamber body 11 is collectively defined by and/or contained within an inner surface of the chamber body 11, a surface of the first semi-permeable membrane 15, and a surface of the second semi-permeable membrane 15. In some embodiments, ingress into and/or egress out of the hollow cavity may be limited to passage through the injection port 13, the first semi-permeable membrane 15, or the second semi-permeable membrane 15.

The semi-permeable membranes 15 can be any suitable shape, size, and/or configuration. For example, the semi-permeable membranes 15 can be porous and configured to permit interchange, ingress, egress, diffusion, and/or passage of select factors (e.g., pharmaceutical and/or biologic products) between the chamber and the subject (e.g., patient, animal, mammal, human, mouse, etc.) once implanted. In some embodiments, the semi-permeable membranes 15 can include, comprise, and/or can be formed of or from any suitable plastic, PTFE (e.g., Teflon™), polyester, and/or any inert or biocompatible material. In some embodiments, such an inert material can be strong, flexible, and able to withstand chemical treatments, sterilization, and/or irradiation. In some embodiments, the semi-permeable membranes are the Durapore® membrane manufactured by MilliporeSigma. In some embodiments, the semi-permeable membranes 15 can be substantially similar to those described in the '961 publication. As described in further detail herein, the arrangement of the biodiffusion chamber 10 can allow the biodiffusion chamber 10 to be at least temporarily stored within a portion of a storage tray and/or other storage device without damaging the semi-permeable membranes.

Biodiffusion Chamber Storage System

FIGS. 2-14 depict a storage system 100 configured to at least temporarily store biodiffusion chambers and/or tools associated with using the biodiffusion chambers, according to an embodiment. In some embodiments, the storage system 100 can be configured to at least temporarily store any suitable device(s) including but not limited to biodiffusion chambers and/or tools associated therewith. In some embodiments, the storage system 100 can be configured to at least temporarily store biodiffusion chambers having any suitable shape, size, and/or configuration. For example, the storage system 100 can be configured to at least temporarily store biodiffusion chambers such as the biodiffusion chamber 10 shown in FIG. 1.

Figure 2:
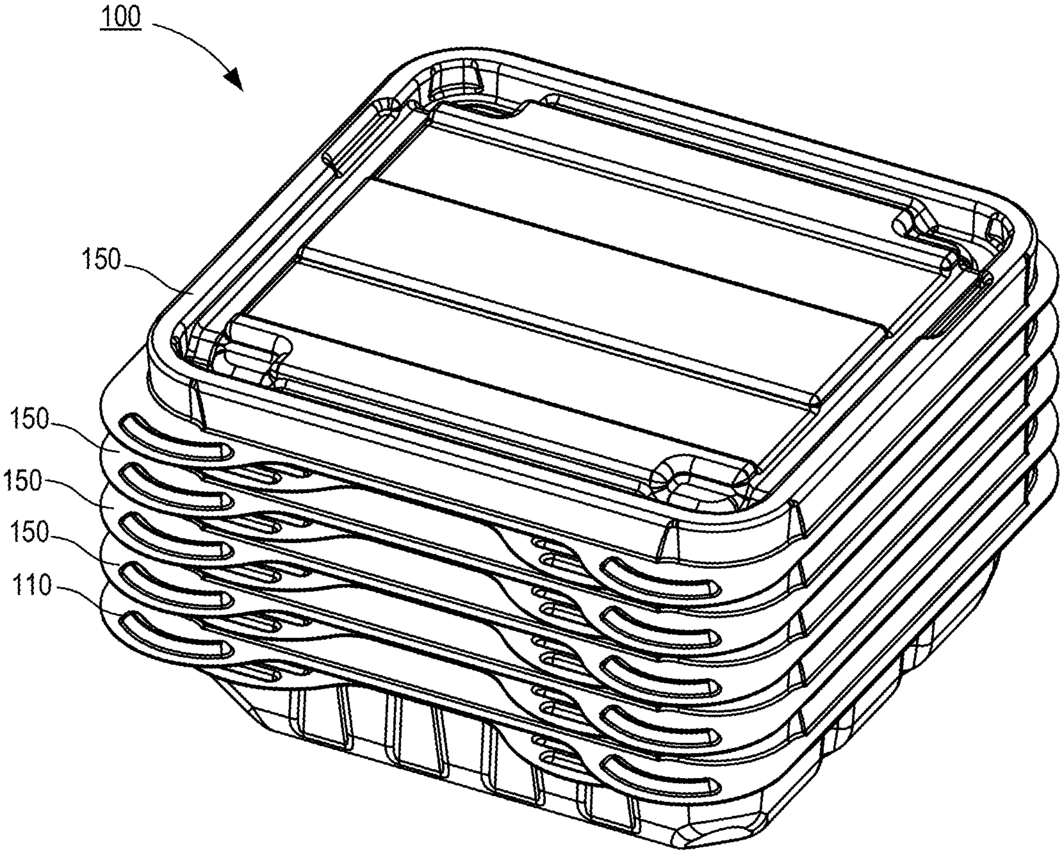
FIG. 2 is a perspective view of a storage system configured to store biodiffusion chambers and/or tools associated with using the biodiffusion chambers according to an embodiment.
Figure 3:
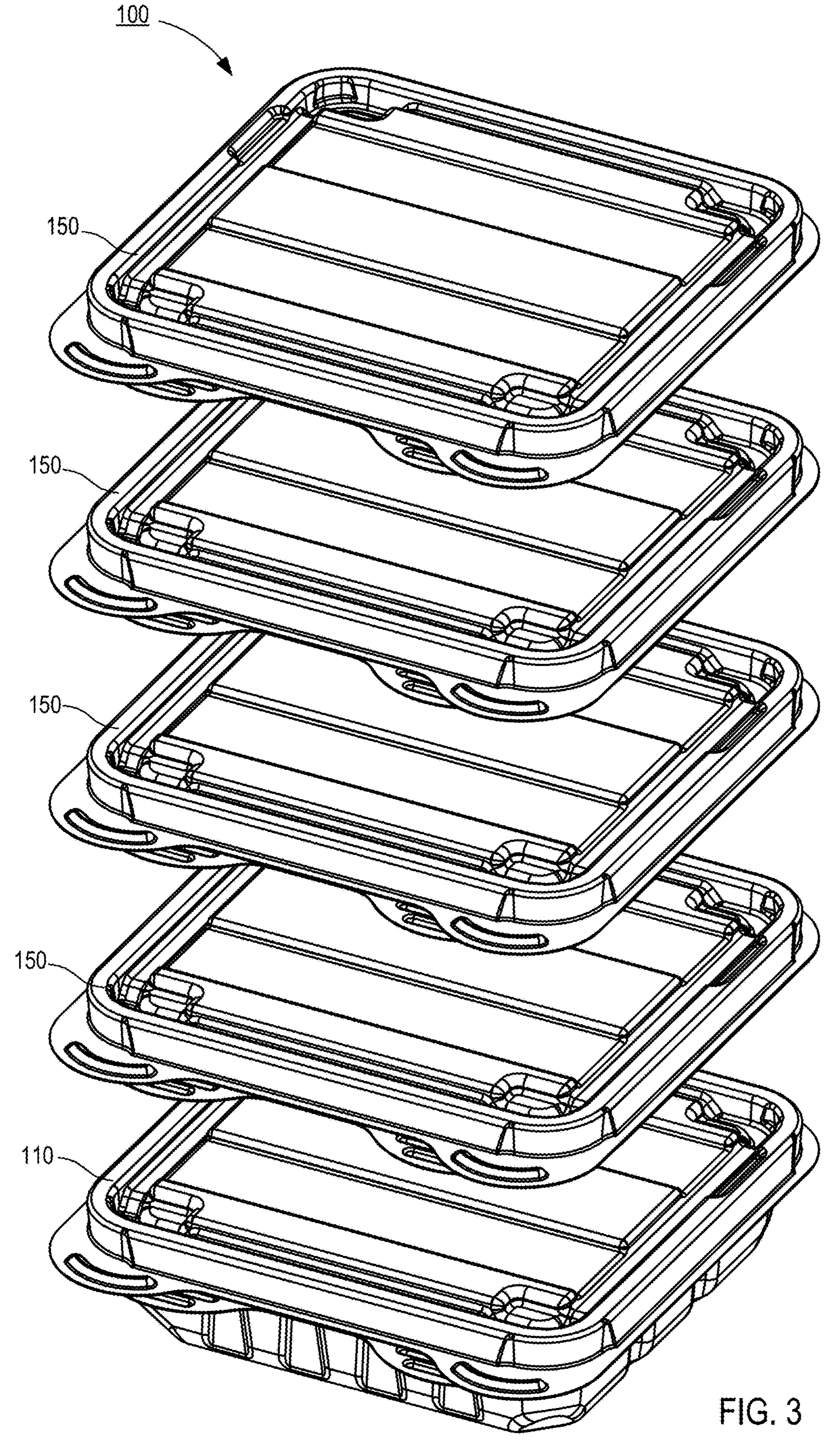
FIG. 3 is a partial exploded perspective view of the storage system of FIG. 2.

As shown in FIGS. 2 and 3, the storage system 100 includes a chamber container 110 and a set of tool containers 150. The chamber container 110 and/or the tool containers 150 can be any suitable shape, size, and/or configuration. In some embodiments, the arrangement of the chamber container 110 and/or the tool containers 150 can allow the containers 110 and/or 150 to be arranged in a stacked configuration. For example, in some embodiments, portions of the containers 110 and/or 150 can allow one or more containers 110 and/or 150 to be at least temporarily coupled together via a friction or interference fit therebetween, as described in further detail herein. The chamber container 110 is configured to at least temporarily store any number of biodiffusion chambers, such as the biodiffusion chamber 10 described with reference to FIG. 1. The tool containers 150 are configured to at least temporarily store any number of tools adapted for use with the biodiffusion chambers disposed in the chamber container 110. In some implementations, the storage system 100 can include multiple tool containers 150 (as shown) such that a number of biodiffusion chambers disposed in the chamber container 110 matches a number tools disposed in the tool containers 150.

FIGS. 4-11 depict the chamber container 110 and/or at least a portion thereof. The chamber container 110 can be any suitable shape, size, and/or configuration. For example, the chamber container 110 can have a substantially rectangular shape. In other embodiments, the chamber container 110 can have any suitable shape. In some embodiments, the shape and/or size of the chamber container 110 can be based at least in part on a shape and/or size of one or more components configured to be disposed therein.

Figure 4:
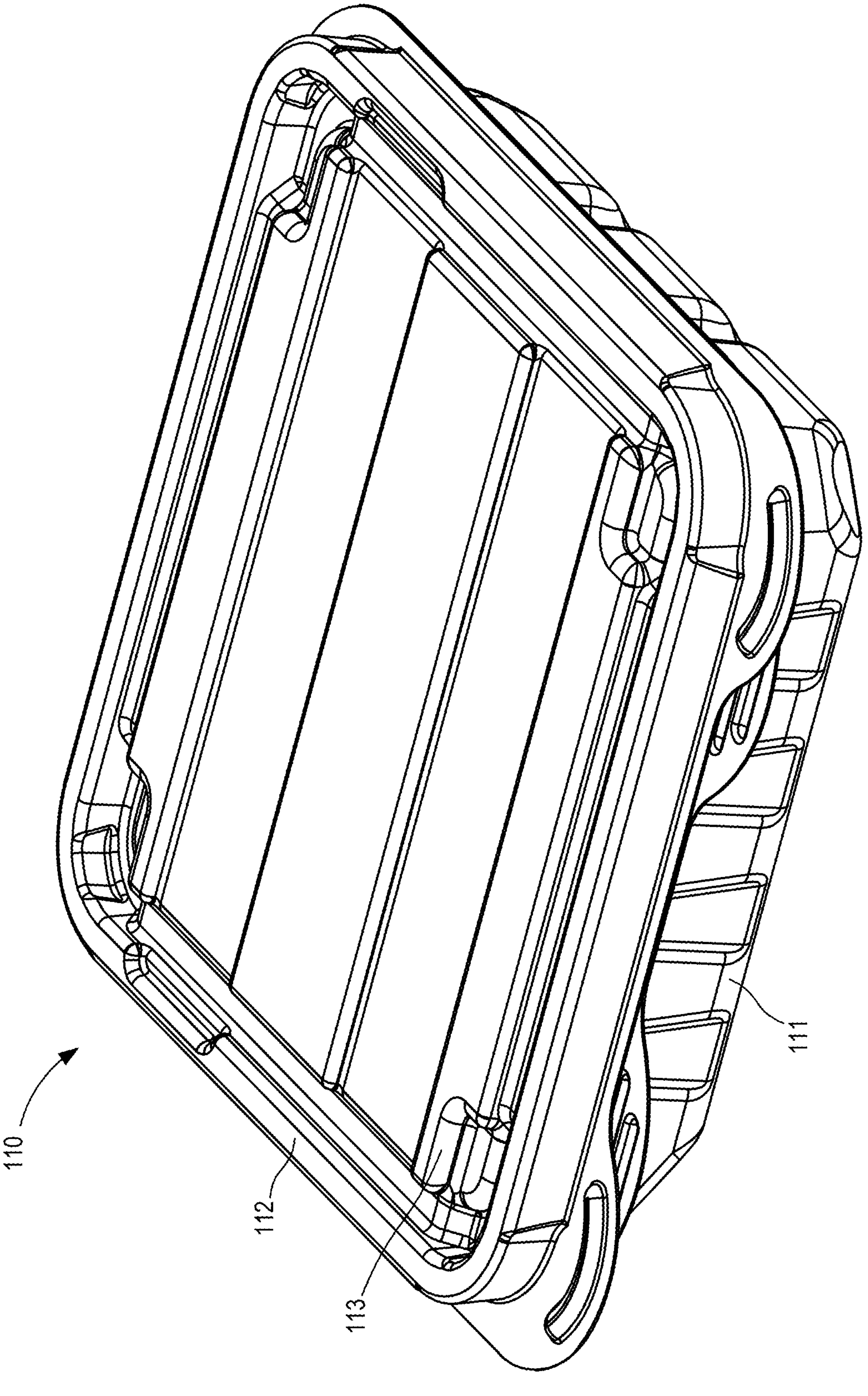
FIG. 4 is a perspective view of a chamber container included in the storage system of FIG. 2.
Figure 5:
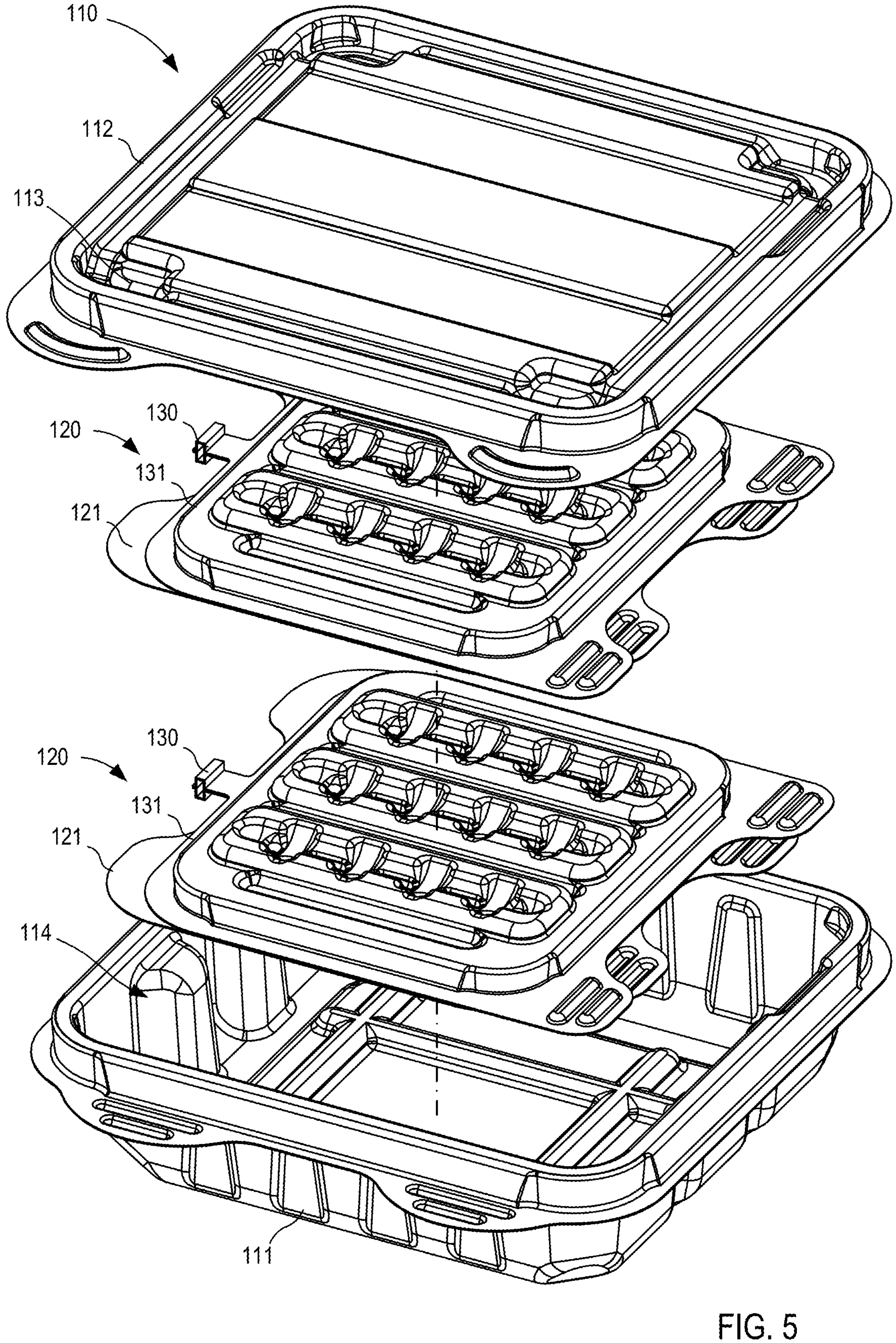
FIG. 5 is a partial exploded perspective view of the chamber container of FIG. 4.
Figure 7:
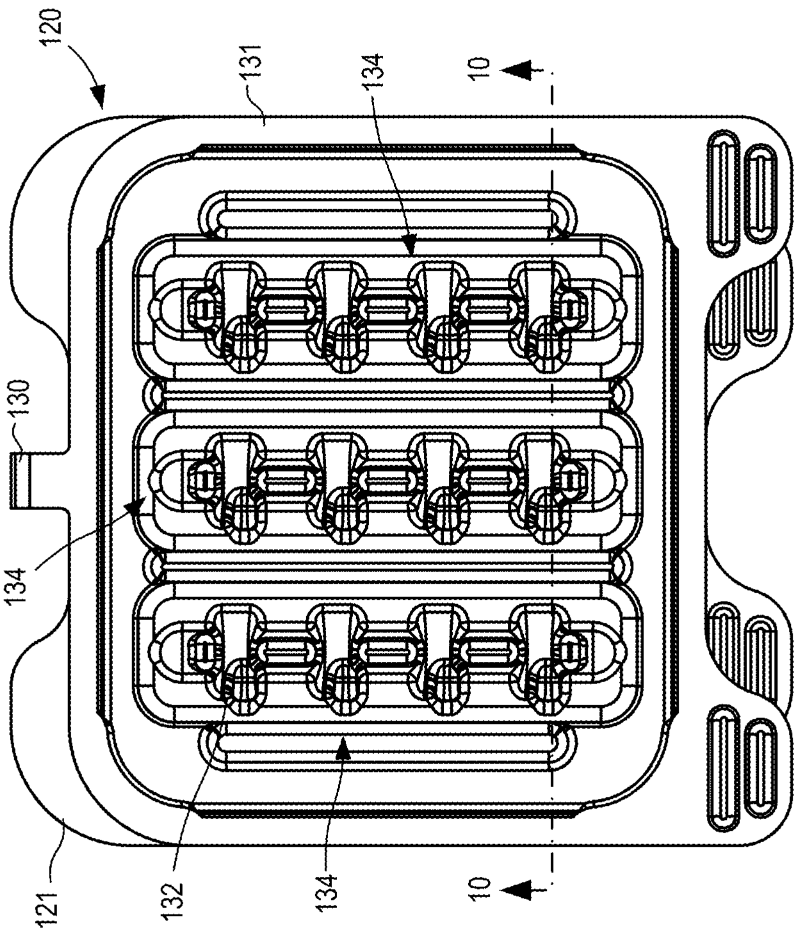
FIGS. 6-9 are a side view, a top view, a front view, and a perspective view of a set of trays included in the chamber container of FIG. 4.
Figure 8:
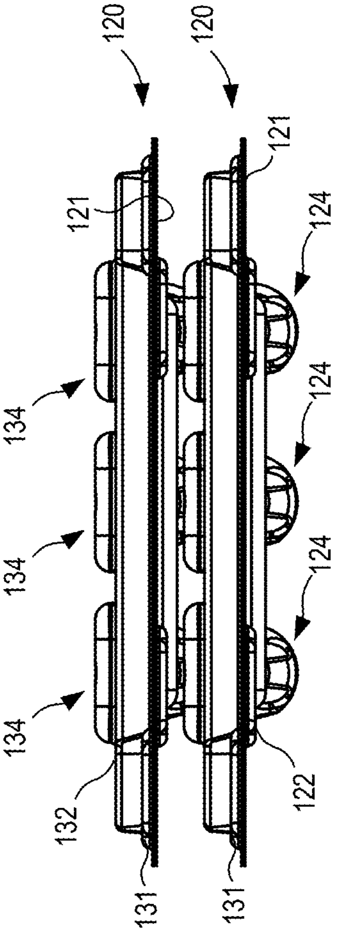
Figure 6:
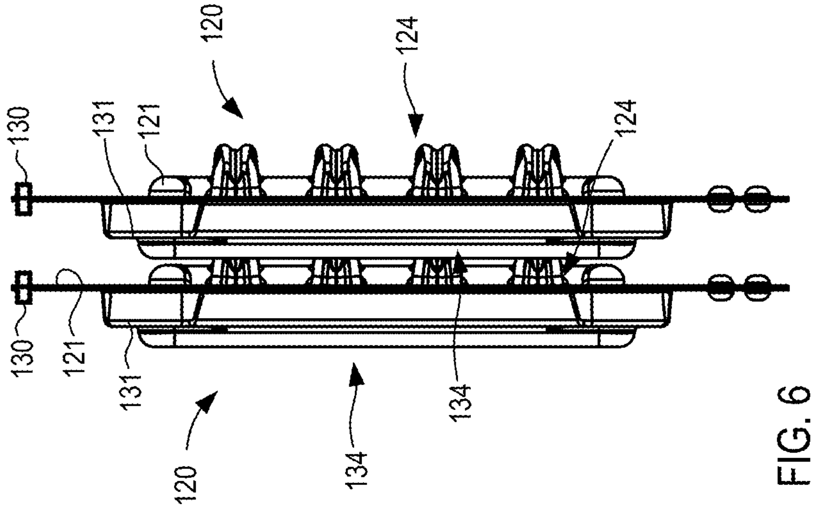
Figure 9:
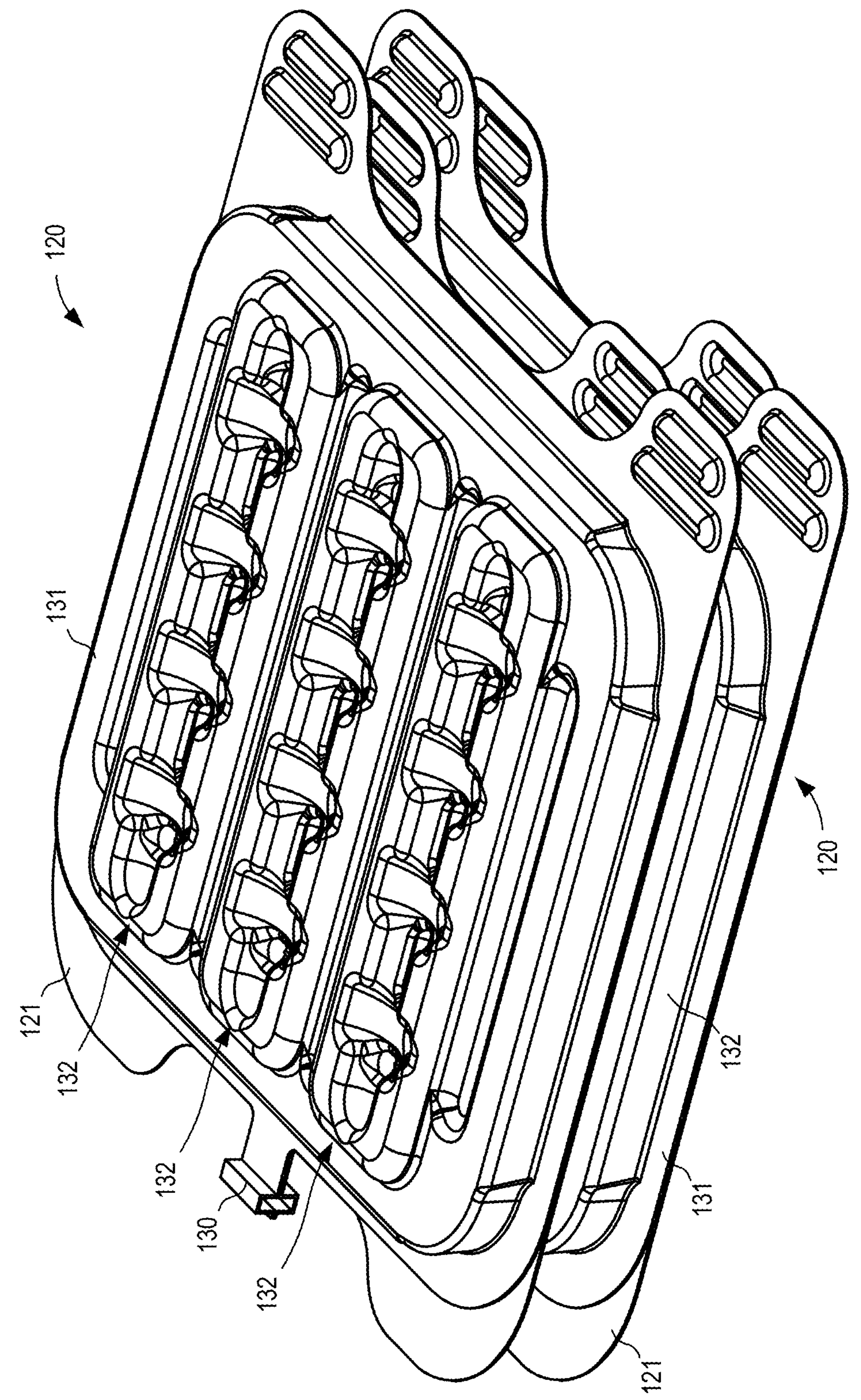

The chamber container 110 includes a base 111 and a lid 112 that collectively define an inner volume 114, as shown in FIGS. 4 and 5. The chamber container 110 is configured to store, at least temporarily, one or more chamber trays 120 within the inner volume 114 (FIG. 5). The base 111 can be, for example, a tub, a tray, a dish, and/or the like. The base 111 can be any suitable shape and/or size. For example, in some embodiments, the shape and/or size of the base 111 can be based at least in part on a shape and/or size of one or more components configured to be disposed within the inner volume 114. Similarly, the base 111 can have any suitable depth. In some implementations, the depth of the base 111 can be modified to, for example, increase or decrease a number of chamber trays 120 that can be at least temporarily stored therein. For example, the chamber container 110 shown in FIGS. 4-11 is configured to receive and/or at least temporarily store two chamber trays 120 within the inner volume 114 (e.g., the base 111 has a sufficient depth to allow two chamber trays 120 to be disposed in the inner volume 114). In other embodiments, however, the base 111 can have a depth sufficient to receive more than two chamber trays 120 (e.g., three trays, four trays, five trays, six trays, seven trays, eight trays, nine trays, ten trays, or more) or less than two chamber trays 120 (i.e., a single chamber tray 120).

The lid 112 is configured to removably couple to the base 111. For example, the lid 112 can be coupled to the base 111 via a friction fit, an interference fit, a press fit, and/or the like. In some embodiments, the lid 112 can be separate from the base 111 and configured to be entirely removable. In other embodiments, at least a portion of the lid 112 can be attached to at least a portion of the base 111 via any suitable coupler such as one or more hinges (e.g., a living hinge), one or more fasteners, and/or the like (or combinations thereof). The lid 112 includes an outer surface 113 that can include one or more features configured to selectively engage with, for example, a portion of one of the tool containers 150 to removably couple the tool container 150 to the chamber container 110. For example, the outer surface 113 of the lid 112 can form one or more recesses, detents, openings, contours, etc. configured to receive and/or otherwise engage with a surface of the tool container 150. In some implementations, such an arrangement can allow the chamber container 110 and the one or more tool containers 150 to be disposed in a stacked configuration.

As described above, the chamber container 110 can be configured to receive and/or at least temporarily store a number of chamber trays 120, as shown in FIG. 5. The chamber trays 120 (also referred to herein as "trays") can be configured to receive, contain, and/or store (at least temporarily) any suitable number of biodiffusion chambers. More particularly, the trays 120 can be configured to receive, contain, and/or store any suitable number of the biodiffusion chambers 10 described above with reference to FIG. 1. In some embodiments, the trays 120 can at least temporarily store between one biodiffusion chamber 10 and twenty biodiffusion chambers 10. In some embodiments, the trays 120 can at least temporarily store 1, 2, 3, 4, 5, 6, 7, 8, 9, 10, 11, 12, 13, 14, 15, 16, 17, 18, 19, or 20 biodiffusion chambers 10. As a specific example, the trays 120 shown in FIGS. 5-11 are configured to store 12 biodiffusion chambers 10. In other embodiments, the trays 120 can at least temporarily store more than 20 biodiffusion chambers 10.

The trays 120 can be any suitable shape, size, and/or configuration and can be formed from any suitable material. For example, in some embodiments, the trays 120 can be formed from a relatively thin material that can be hollow and/or can be shapes to define an inner region configured to at least temporarily store the biodiffusion chambers 10. In some embodiments, the relatively thin material can allow at least a portion of the trays 120 to be relatively flexible and/or movable while providing sufficient stiffness to support the biodiffusion chambers 10 disposed therein. In some embodiments, the relatively thin material can be a biocompatible material such as any of those described above. For example, the biocompatible material can be a biocompatible plastic and/or the like. In other embodiments, the trays 120 can be formed from any other suitable material including, for example, non-biocompatible materials.

Each tray 120 included in and/or configured to be disposed in the chamber container 110 can be the same or can be different. For example, in some embodiments, the chamber container 110 can include and/or can receive a first tray and a second tray. The first tray can be configured to store biodiffusion chambers having a first size and the second tray can be configured to store biodiffusion chambers having a second size different from the first size. In such embodiments, a size of the first tray can be different from a size of the second tray. In this embodiment, however, the trays 120 included in and/or configured to be disposed in the chamber container 110 have substantially the same shape and size. Accordingly, while two trays 120 are shown in FIGS. 5-11, a detailed discussion of a single tray 120 is provided below and is intended to apply equally to both trays 120 unless clearly stated otherwise.

The tray 120 includes a first portion 121 and a second portion 131 that is movably and/or removably coupled to the first portion 121. For example, the first portion 121 and the second portion 131 can be formed separately and coupled together via a friction fit, an interference fit, a press fit, and/or the like, as described above with reference to the chamber container 110. In some embodiments, the first portion 121 and the second portions 131 can be monolithically and/or unitarily formed, as shown in FIGS. 5-11. In such embodiments, the tray 120 can include a hinge 130 (e.g., a living hinge or the like) that can allow the first portion 121 and the second portion 131 to be coupled while also allowing for pivoting motion between the first portion 121 and the second portion 131. The arrangement of the hinge 130 can allow the tray 120 to be transitioned between a closed configuration (shown in FIGS. 5-11) and an open configuration (not shown). For example, the hinge 130 can allow the second portion 131 to be pivoted about an axis defined by the hinge 130 and relative to the first portion 121, and/or vice versa. As such, in some embodiments, the tray 120 can be similar to, or can have a form that is similar to, some known "clamshell" arrangements.

While the hinge 130 is particularly shown in FIGS. 5-9, it should be understood that the tray 120 can include a living hinge having any suitable shape and/or size, and/or can include any other suitable hinge, coupler, connector, etc. In some such embodiments, the hinge, coupler, connector, etc. can be monolithically and/or unitarily formed with one or both of the first portion 121 and the second portion 131. In other embodiments, the first portion 121, the second portion 131, and the hinge, coupler, connector, etc. can be formed independently and later coupled (e.g., during manufacturing or by an end user).

Figure 10:
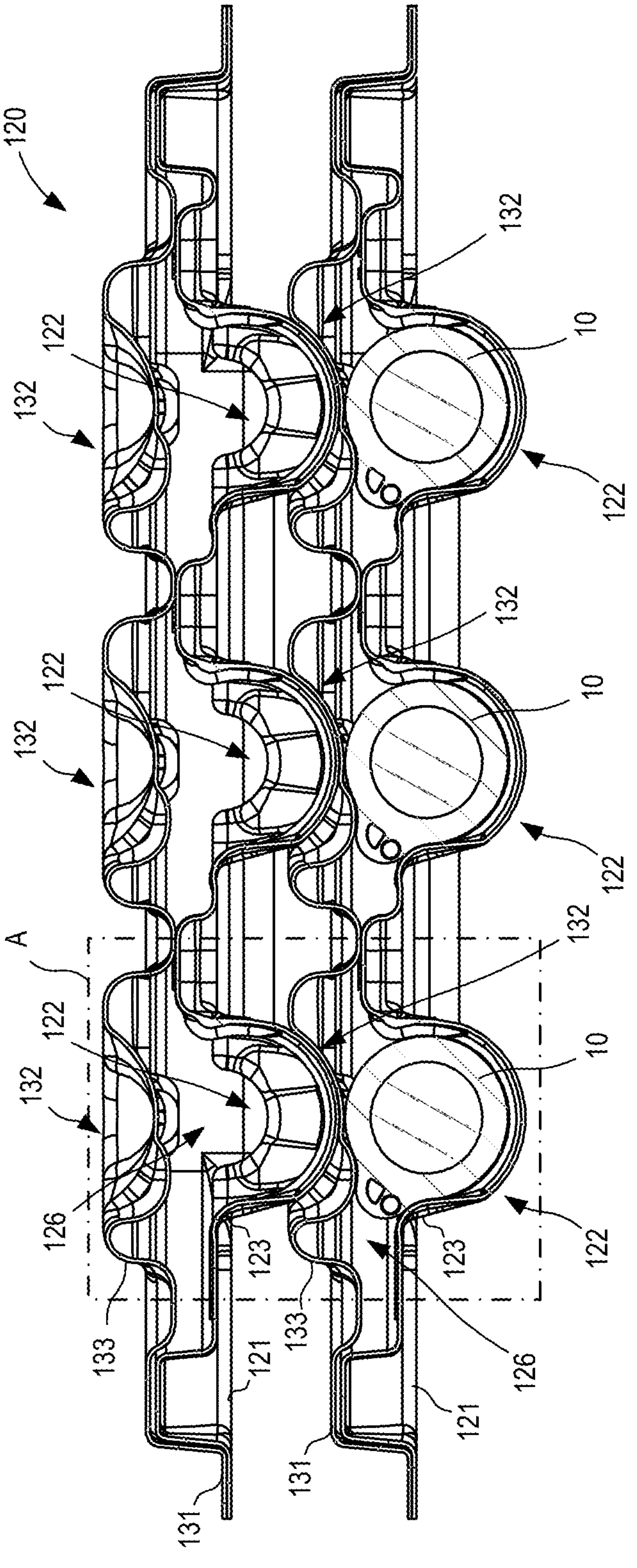
FIG. 10 is a cross-sectional view of the set of trays of FIGS. 6-9, taken along the line 10-10 in FIG. 7.
Figure 11:
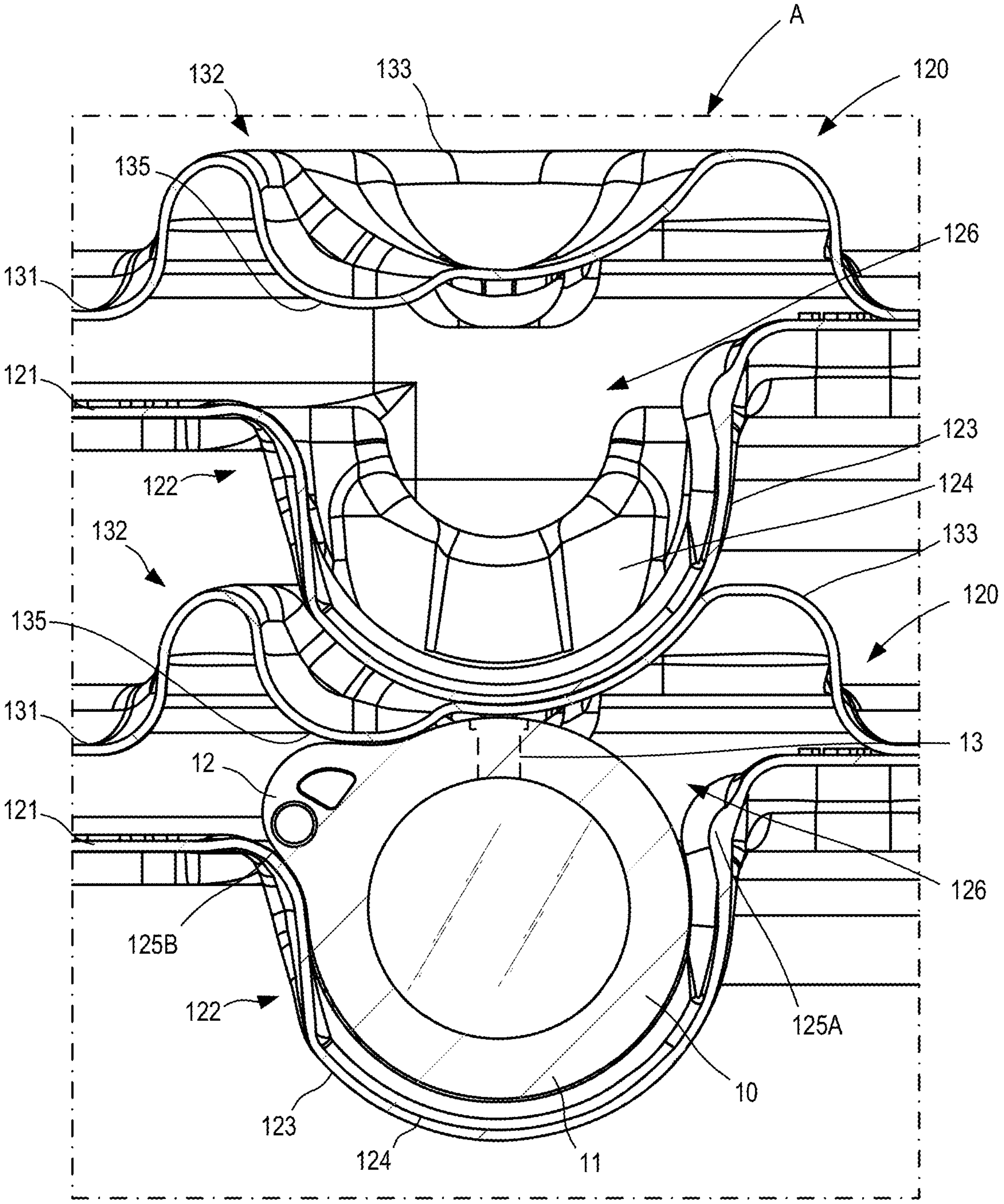
FIG. 11 is an enlarged cross-sectional view of a portion of the set of trays identified in FIG. 10 as region A.

The first portion 121 of the tray 120 has a set of chambers regions 122 that have and/or the form a contour 123. Similarly, the second portion 131 of the tray 120 has a set of chambers regions 132 that have and/or the form a contour 133. The arrangement of each tray 120 can be configured to allow two or more trays 120 to be disposed in a stacked arrangement (e.g., when contained in the chamber container 110). More specifically, the contours 123 and 133 of the chamber regions 122 and 132, respectively, can have a shape, size, and configuration that are at least partially similar, related, matching, mating, and/or the like. As shown in FIGS. 10 and 11, the chamber regions 122 and 132 and/or at least the contours 123 and 133 thereof can be configured such that an outer surface that has and/or that at least partially forms the contour 123 of the first portion 121 of a first tray 120 (e.g., the top tray 120 shown in FIGS. 6-11) is in at least partial contact with an outer surface that has and/or that at least partially forms the contour 133 of the second portion 131 of the second tray 120 (e.g., the bottom tray 120 shown in FIGS. 6-11). Said another way, at least a portion of the outer surface forming the contour 133 of the second portion 131 of the second tray 120 can have and/or can form a concave recess or detent, thereby allowing a substantially convex portion of the outer surface forming the contour 123 of the first portion 121 of the first tray 120 to be disposed therein when the first tray 120 is stacked on the second tray 120.

As shown in FIGS. 6-11, the tray 120 can be configured such that the sets of chamber regions 122 and 132 are substantially aligned and arranged in rows. For example, in this embodiment, the first portion 121 and the second portion 131 each include three rows of corresponding and/or aligned chambers regions 122 and 132, respectively. In other embodiments, the tray 120 can include fewer than three rows of corresponding and/or aligned chamber regions 122 and 132 (e.g., one or two rows) or more than three rows of corresponding and/or aligned chamber regions 122 and 132 (e.g., four, five, six, seven, eight, nine, or ten rows, or more).

Each corresponding and/or aligned pair of the chamber regions 122 and 132 collectively defines an inner volume 126 configured to receive one or more biodiffusion chambers 10. For example, in this embodiment, each inner volume 126 is configured to receive and/or at least partially store four biodiffusion chambers 10 arranged in a line along a length of the associated chamber regions 122 and 132. More particularly, the contour 123 of each chamber region 122 of the first portion 121 can include, form, and/or define one or more seats 124 configured to receive at least a portion of a biodiffusion chamber 10. In this embodiment, the contour 123 of each chamber region 122 forms four seats 124 and thus, the inner volume 126 of each chamber region 122 is configured to receive four biodiffusion chambers 10. In other embodiments, the contour 123 of each chamber region 122 can include fewer than four seats (e.g., one, two, or three seats 124) or more than four seats (e.g., five, six, seven, eight, nine, ten, or more seats 124. Said another way, each inner volume 126 defined by the corresponding and/or aligned chamber regions 122 and 132 can receive and/or store fewer than four biodiffusion chambers 10 (e.g., one, two, or three biodiffusion chambers 10) or more than four biodiffusion chambers 10 (e.g., five, six, seven, eight, nine, or ten biodiffusion chambers 10, or more).

In some embodiments, the contours 123 and 133 of the chamber regions 122 and 132, respectively, can be configured such that one or more inner surfaces of the tray 120 selectively contacts and/or engages one more portions of each biodiffusion chamber 10 disposed in the inner volumes 126. For example, as shown in FIG. 11, the contour 123 can have and/or can form at least a first retention surface 125A and a second retention surface 125B that are configured to contact the biodiffusion chamber 10 in a predetermined manner. Similarly, the contour 133 can have and/or can form one or more retention surfaces 135 that is/are configured to contact the biodiffusion chamber 10 in a predetermined manner. In some embodiments, the retention surfaces 125A, 125B, and/or 135 can contact and/or engage the biodiffusion chamber 10 to at least temporarily maintain the biodiffusion chamber 10 in a fixed and/or desired position, orientation, and/or the like.

In this embodiment, the first retention surface 125A and the second retention surface 125B are positioned on opposite sides of each seat 124. The first retention surface 125A can be configured to contact and/or engage a portion of the biodiffusion chamber 10 as it is being placed in the seat 124. In some embodiments, the cylindrical and/or curved shape of the biodiffusion chamber 10 can be such that once the biodiffusion chamber 10 is in a desired or resting position in or on the seat 124, the first retention surface 125A is spaced apart from and/or otherwise is not in contact with the biodiffusion chamber 10. Said another way, in some embodiments, the first retention surface 125A can be configured to contact the biodiffusion chamber 10 as the biodiffusion chamber 10 is being placed in or removed from the seat 124 without necessarily being in contact with the biodiffusion chamber 10 when it is disposed in or resting on the seat 124. In some implementations, such an arrangement can result in the first retention surface 125A forming a locking or retaining mechanism configured to retain the biodiffusion chamber 10 in the seat 124 until a force is exerted on the biodiffusion chamber 10 that is sufficient to overcome a friction force between the first retention surface 125A and a surface of the biodiffusion chamber 10.

As shown in FIG. 11, the biodiffusion chamber 10 can be inserted into and/or disposed on each seat 124 formed by the contour 123 and can be positioned and/or oriented such that the second retention surface 125B is in contact with a portion of the biodiffusion chamber 10 at or near the flange 12 of the biodiffusion chamber 10. In some embodiments, the second retention surface 125B can be formed on a second side of the seat 124 opposite the first retention surface 125A. In some embodiments, the second retention surface 125B can be, for example, a shoulder or the like between the seat 124 and a substantially non-curved or non-contoured portion of the chamber region 122. In some embodiments, the second retention surface 125B can have a radius of curvature that is based at least in part on a radius of curvature between the flange 12 and the substantially cylindrical portion of the biodiffusion chamber 10.

The retention surface 135 of the chamber regions 133 is configured to contact the biodiffusion chamber 10 when the tray 120 is in the closed state or configuration. For example, as described above, the first portion 121 and the second portion 131 of the tray 120 are coupled together (e.g., via the hinge 130) and configured to allow for relative movement therebetween. In some implementations, the second portion 131 of the tray 120 can be placed in a position relative to the first portion 121 to place the tray 120 in the open state or configuration (not shown). In some instances, a biodiffusion chamber 10 can be placed in or on each seat 124 while the tray 120 is in the open state or configuration. Once the biodiffusion chamber 10 is in a desired position and/or orientation, the second portion 131 can be moved relative to the first portion 121 to place the tray 120 in the closed state and/or configuration. As described above with reference to the retention surface 125B, the retention surface 135 of the second portion 131 is configured to engage and/or contact a portion of the biodiffusion chamber 10 at or near the flange 12 of the biodiffusion chamber 10. In some embodiments, the second retention surface 125B of the first portion 121 and the retention surface 135 of the second portion 131 can be in contact with opposite sides of the flange 12, as shown in FIG. 11. As such, the second retention surface 125B of the first portion 121 and the retention surface 135 of the second portion 131 can be in contact with the biodiffusion chamber 10, thereby limiting and/or restricting movement of the biodiffusion chamber 10.

As described above, the first retention surface 125A can be configured to contact a portion of the biodiffusion chamber 10 while the biodiffusion chamber 10 is inserted into and/or removed from the seat 124, thereby at least temporarily retaining the biodiffusion chamber 10 in a desired position (or a desired or acceptable range of positions) in or relative to the seat 124. The second retention surface 125B of the first portion 121 and the retention surface 135 of the second portion 131 can be configured to engage the biodiffusion chamber 10 to at least partially limit and/or restrict movement (e.g., rotation) of the biodiffusion chamber 10 when disposed in the seat 124. In some implementations, the retention surfaces 125A, 125B, and/or 135 can place and/or maintain the biodiffusion chamber 10 in a position and/or orientation such that the injection portion 13 of the biodiffusion chamber 10 is accessible. For example, as shown in FIG. 11, the retention surfaces 125A, 125B, and/or 135 can position and/or orient the biodiffusion chamber 10 such that the injection port 13 is substantially perpendicular to one or more flat surfaces of the tray 120 and/or a surface on which the tray 120 is sitting. Said another way, the biodiffusion chamber 10 can be positioned and/or oriented such that the injection port 13 is in a vertical or substantially vertical orientation.

In some instances, placing the biodiffusion chamber 10 in the position and/or orientation shown in FIG. 11 can allow a user to inject any suitable fluid and/or composition into the biodiffusion chamber 10 without having to remove the biodiffusion chamber 10 from the tray 120 (or at least the first portion 121 of the tray 120). For example, in use, an end user such as a doctor, surgeon, technician, etc. can open the tray 120 (e.g., by pivoting the second portion 131 relative to the first portion 131), thereby placing the tray 120 in the open state and/or configuration. With the tray 120 in the open state and/or configuration, the biodiffusion chambers 10 can still be disposed in or on the seats 124 and the retention surfaces 125A and 125B can still retain and/or maintain the biodiffusion chambers 10 in the desired position and/or orientation shown in FIG. 11. Accordingly, the injection ports 13 can be readily accessible, thereby allowing the end user to manipulate a pipette or other suitable transfer device to transfer fluids and/or compositions into the biodiffusion chamber 10 via the injection port 13.

The tool container(s) 150 of the storage system 100 is/are described below with reference to FIGS. 12-14. Each tool container 150 included in the storage system 100 is configured to at least temporarily store a number of tools 170 adapted for use with the biodiffusion chambers disposed in the chamber container 110. In some implementations, the storage system 100 can include multiple tool containers 150 (as shown in FIG. 2) such that the number of tools 170 disposed in the tool container(s) 150 matches the number of biodiffusion chambers 10 disposed in the chamber container 110. For example, each tool containers 150 can be configured to receive and at least temporarily store six tools 170 (see e.g., FIGS. 13 and 14) and the storage system 100 can be configured to include four tool containers 150. Accordingly, the storage system 100 can include 24 tools 170, with each tool 170 corresponding to a single biodiffusion chamber 10 included in one of the two trays 120 configured to be disposed or at least temporarily contained in the chamber container 110. In some embodiments, each tool container 150 included in the storage system 100 can be substantially the same. Thus, while the storage system 100 is shown in FIGS. 2 and 3 as including four tool containers 150, a detailed discussion of the single tool container 150 shown in FIGS. 12-14 is provided below and is intended to apply equally to each of the tool containers 150 included in the storage system 100 unless clearly stated otherwise.

The tool container 150 can be any suitable shape, size, and/or configuration. For example, the tool container 150 can have a substantially rectangular shape that can be similar to and/or based at least in part on a size and/or shape of the chamber container 110. In some embodiments, the shape and/or size of the tool container 150 can be based at least in part on a shape and/or size of one or more tools 170 configured to be disposed therein.

Figure 12:
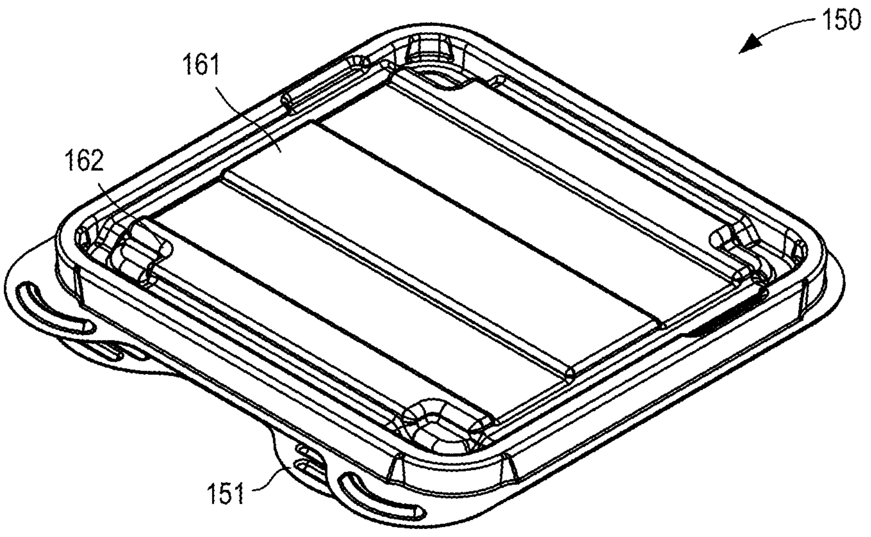
FIG. 12 is a perspective view of a tool container included in the storage system of FIG. 2.
Figure 13:
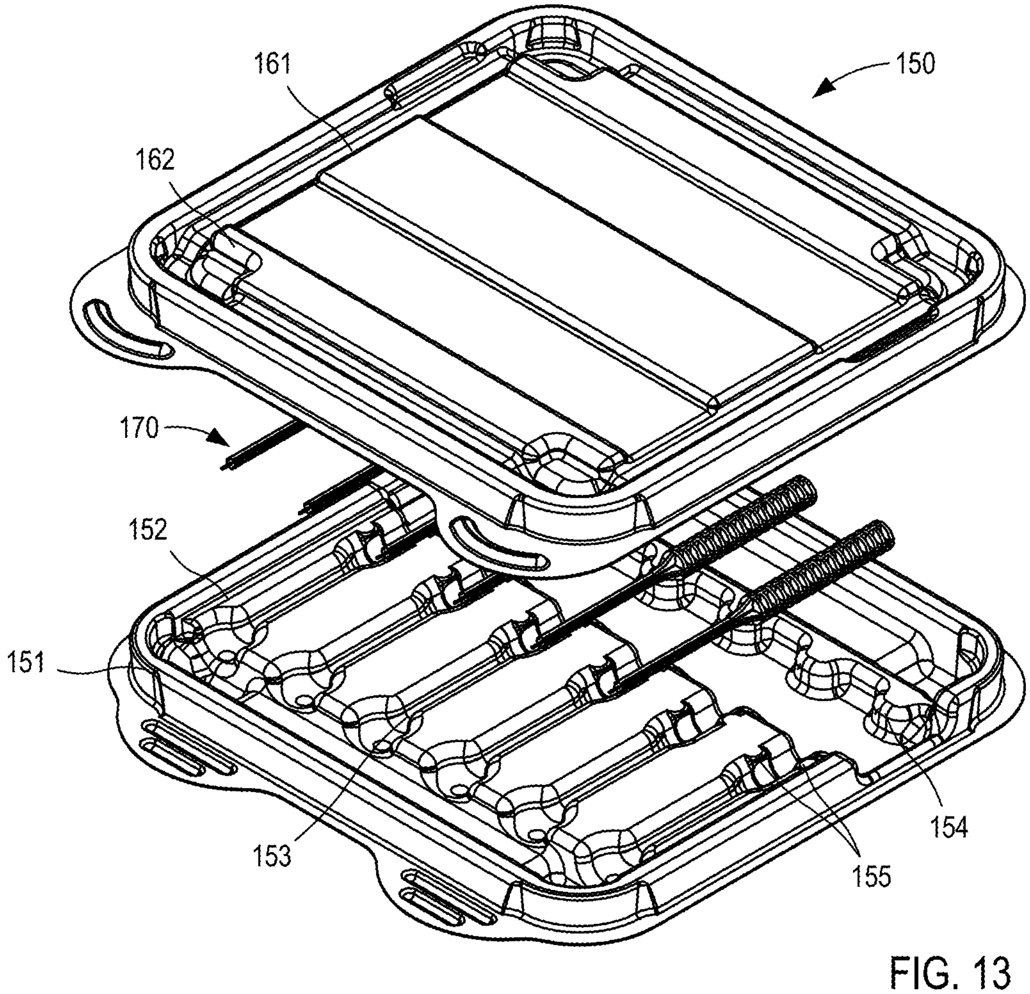
FIG. 13 is a partial exploded perspective view of the tool container of FIG. 12.
Figure 14:
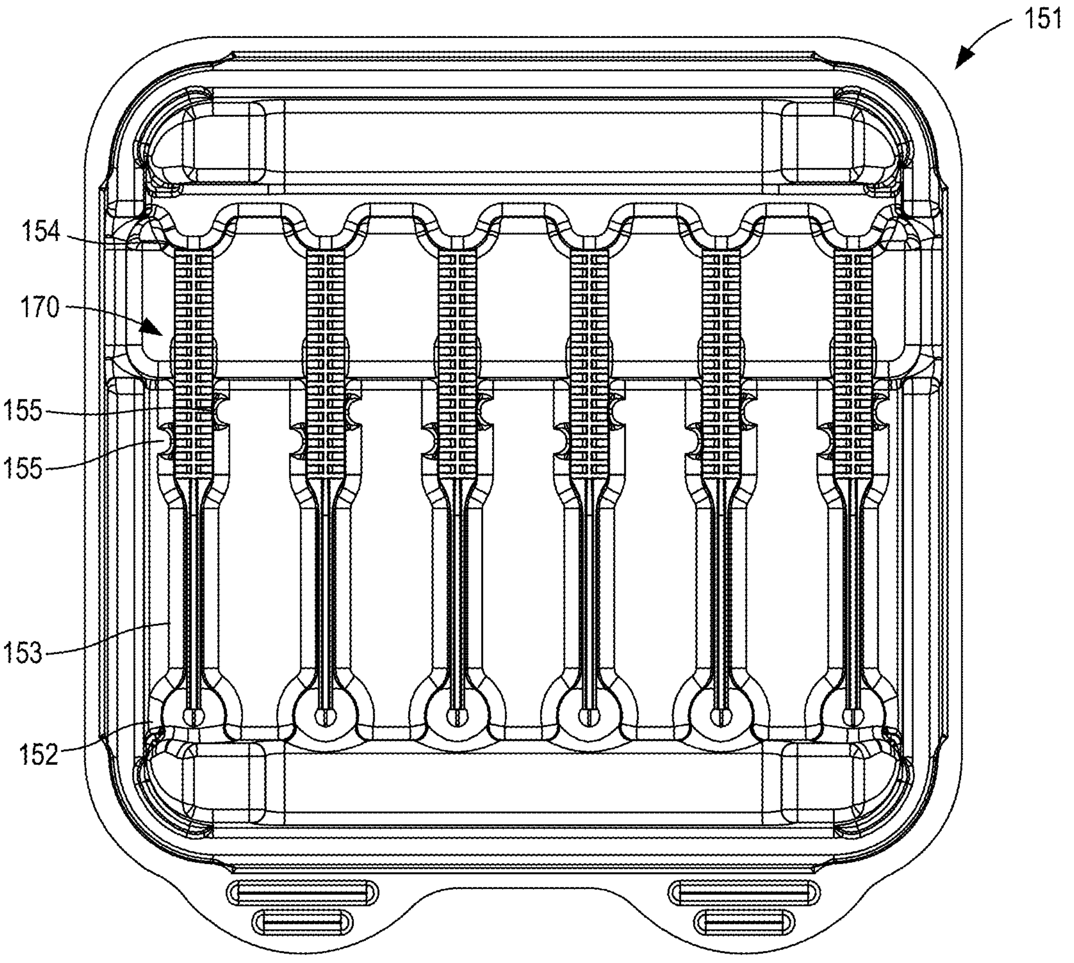
FIG. 14 is a top view of a base of the tool container of FIG. 12 shown as being coupled to a set of tools.

As shown in FIGS. 12-14, the tool container 150 includes a base 151 and a lid 161 removably coupleable to the base 151. For example, the lid 161 can be coupled to the base 151 via a friction fit, an interference fit, a press fit, and/or the like. In some embodiments, the lid 161 can be separate from the base 151 and configured to be entirely removable. In other embodiments, at least a portion of the lid 161 can be attached to at least a portion of the base 151 via any suitable coupler such as one or more hinges (e.g., a living hinge), one or more fasteners, and/or the like (or combinations thereof). The lid 161 includes an outer surface 162 that can include one or more features configured to selectively engage with, for example, a portion of one of the other tool containers 150 included in the storage system 100. For example, the outer surface 162 of the lid 161 can form one or more recesses, detents, openings, contours, etc. configured to receive and/or otherwise engage with an outer surface of the base 151 of one of the other tool containers 150. In some implementations, such an arrangement can allow the set tool containers 150 (see e.g., FIGS. 2 and 3) to be disposed in a stacked configuration.

The base 151 of the tool container 150 can be any suitable shape, size, and/or configuration. For example, in some embodiments, the shape and/or size of the base 151 can be based at least in part on a shape and/or size of one or more of the tools 170 configured to be disposed in the tool container 150. More particularly, the base 151 includes an inner surface 152 that has and/or that forms any number of tool regions 153. For example, as shown in FIG. 14, the inner surface 152 of the base 151 can have and/or can form six tool regions 153, each of which is configured to receive and/or at least temporarily couple to one of the tools 170. In some embodiments, each of the tool regions 153 can be a recessed or contoured surface having a size and/or shape that is based at least in part on a size and/or shape of the tool 170.

Each of the tool regions 153 includes and/or forms a backstop 154 and a set of retention surfaces 155. As shown in FIGS. 13 and 14, a back surface or end of a tool 170 can be placed in contact with the backstop 154 when the tool 170 is disposed in one of the tool regions 153. The retention surfaces 155 can be, for example, protrusions, bumps, tabs, knobs, etc. configured to contact and/or otherwise engage opposing sides of the tool 170. In some implementations, the retention surfaces 155 can be configured to form a press fit, snap fit, friction fit, interference fit, etc. with a portion of the tool 170 that is operative to retain or maintain the tool 170 in the corresponding tool region 153. For example, in some embodiments, a friction force resulting from the retention surfaces 155 contacting the portions of the tool 170 can be sufficient to removably couple the tool 170 to the base 151 until a user removes the tool 170 by exerting a force sufficient to overcome the friction force.

Figure 15:
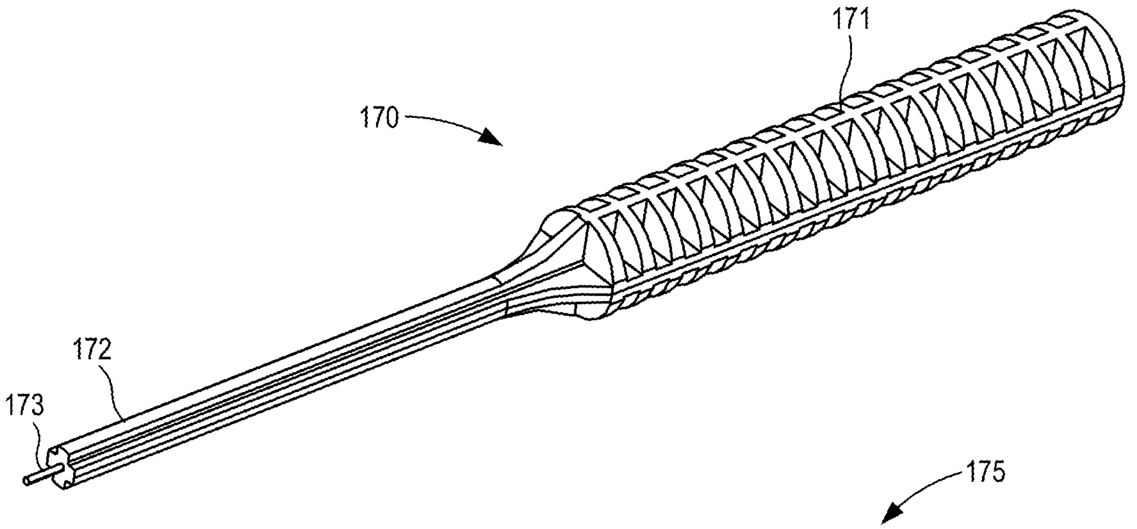
FIG. 15 is a perspective view of a tool included in the tool container of FIG. 12.
Figure 16:
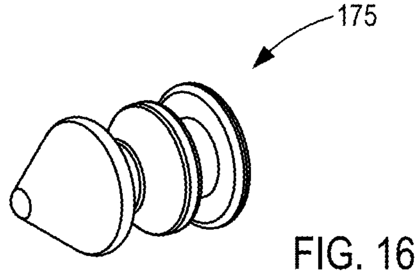
FIG. 16 is a perspective view of a seal that can be coupled to a portion of the tool of FIG. 15.
Figure 17:
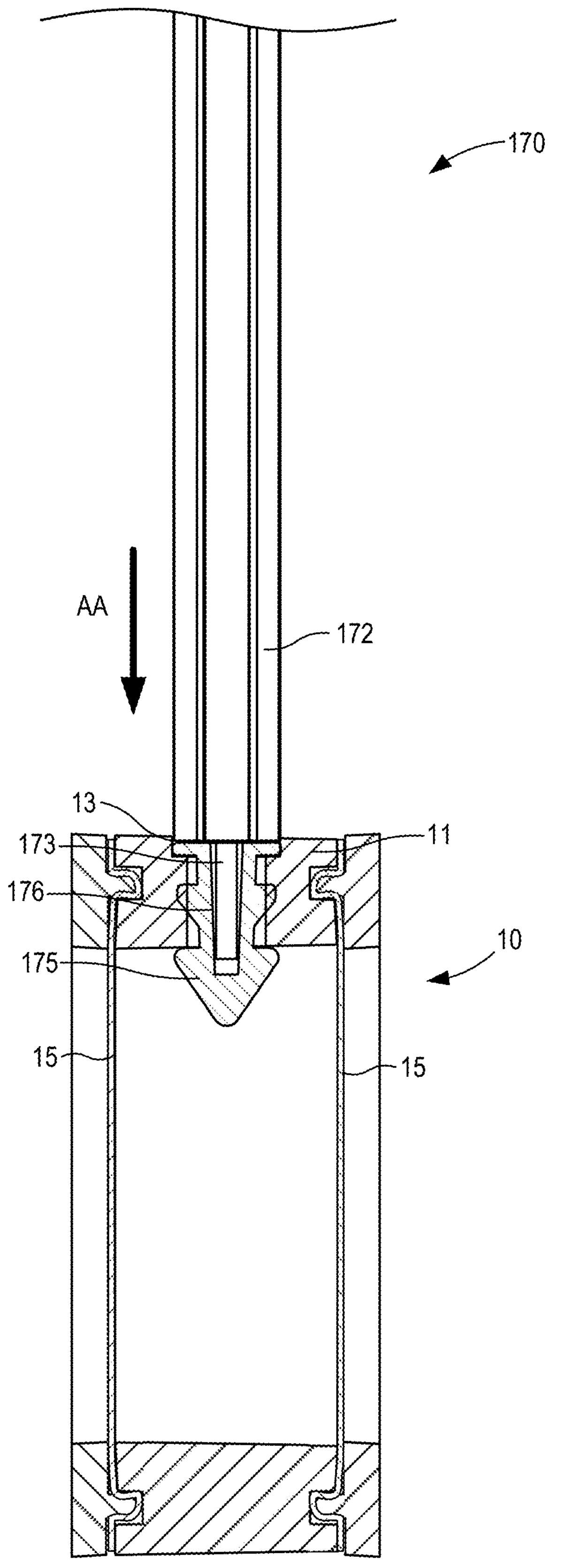
FIG. 17 is an enlarged cross-sectional view of a portion of the tool of FIG. 15 coupled to the seal of FIG. 16 inserted in an injection port.

The tools 170 can be adapted for use with the biodiffusion chambers 10. In some embodiments, the tools 170 can be disposable or single use. In other embodiments, the tools 170 can be reusable. For example, as shown in FIGS. 15-17, the tools 170 can be used to insert a seal member 175 into the injection port 13 of a biodiffusion chamber 10 after conveying a fluid and/or composition into the biodiffusion chamber 10. More particularly, as shown in FIG. 15, the tool 170 can include a proximal end portion 171 and a distal end portion 172. The proximal end portion 171 of the tool 170 can be a handle or the like that can be grasped by a user during use. The distal end portion 172 of the tool 170 can be and/or can include, for example, a coupling member 173 that can be coupled to the seal member 175 (see e.g., FIGS. 16 and 17). In some embodiments, the coupling member 173 can be, for example, a relatively thin rod, post, extension, and/or the like configured to be at least partially inserted into an opening 176 defined by the seal member 175. In some embodiments, the tool 170 and/or the seal member 175 can be substantially similar to any of the tools and/or seal members, respectively, described in the '961 publication. In other embodiments, the tool 170 and/or the seal member 175 can have any suitable configuration and/or arrangement. In some embodiments, the tool 170 can be coupled to the seal member 175 during a manufacturing process and then disposed within the corresponding tool region 153 of the tool container 150. In other embodiments, the tool 170 can be coupled to the seal member 175 by an end user (e.g., the end user can remove the tool 170 from the tool container 150 can couple the tool 170 to the seal member 175 via the coupling member 173).

As described above, the trays 120 of the storage system 100 can be configured to at least temporarily store the biodiffusion chamber 10 in a predetermined and/or desired orientation that can, for example, facilitate the filling and/or sealing of the biodiffusion chamber 10. For example, in some implementations, a user (e.g., doctor, physician, surgeon, technician, nurse, etc.) can place one or more of the trays 120 in the open state and/or configuration, thereby gaining access to the biodiffusion chambers 10 contained therein. As described in detail above, the orientation of each of the biodiffusion chambers 10 disposed in the seats 124 of the tray 120 can allow the user convey any desired fluid, composition, etc. through the injection port 13 and into the inner volume of the biodiffusion chambers 10 (e.g., via a pipette or other suitable transfer device) without having to manipulate, move, and/or otherwise reorient the biodiffusion chambers 10. In some embodiments, the fluid, the composition, and/or the method of filling the biodiffusion chambers 10 can be substantially similar to any of those described in the '961 publication.

After conveying the desired fluid and/or composition into one or more of the biodiffusion chambers 10, the user can manipulate the tool 170 to insert the seal member 175 into the injection port 13 of the one or more biodiffusion chambers 10 while the one or more biodiffusion chambers 10 are still disposed in the corresponding seats 124 of the tray 120. For example, in some embodiments, the coupling member 173 can be pressed into the opening 176 of the seal member 175 such that a friction force therebetween at least temporarily couples the seal member 175 to the tool 170. Said another way, a friction force between the coupling member 173 and a surface of the seal member 175 defining the opening 176 can be sufficient to at least temporarily maintain the seal member 175 in a substantially fixed position relative to the tool 170. As such, the user can exert a force on the tool 170 to insert the seal member 175 into the injection port 13, as indicated by the arrow AA in FIG. 17. When disposed in the injection port 13, the seal member 175 can selectively engage a surface or portion of the injection port 13 and/or any other suitable surface or portion of the biodiffusion chamber 10 such that a force (e.g., a friction force) defined therebetween is greater than a friction force between the coupling member 173 and the surface of the seal member 175 that defines the opening 176. Thus, when the user moves the tool 170 in a direction opposite the direction of insertion (e.g., opposite the arrow AA), the coupling member 173 can be removed from the opening of the seal member 175 without removing the seal member 175 from the injection port 13. In this manner, the user can fill and seal the biodiffusion chambers 10 while the biodiffusion chambers 10 are disposed in the trays 120. Once filled and sealed, the biodiffusion chambers 10 can be removed from the trays 120 and, for example, inserted into the body of a subject or patient via any suitable surgical method or the like.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. For example, while the biodiffusion chamber 10 is described above with reference to FIG. 1, in other embodiments, the biodiffusion chamber 10 can be any of those described, for example, in the '961 publication and/or any other suitable chamber. As another example, while the coupling member 173 of the tool 170 is shown and described as being a relatively thin rod, post, extension, etc. configured to at least temporarily couple the tool 170 to the seal member 175, in other embodiments, a tool can include any suitable coupling member or mechanism configured to at least temporarily couple the tool to the seal member. As another example, while the storage system 100 is described above as including multiple tool containers 150, each having multiple tools 170 (e.g., one tool 170 for each biodiffusion chamber 10), in other embodiments, the storage system 100 can include a single reusable tool that can be provided with the chamber container 110 or independent of the chamber container 110.

Although various embodiments have been described as having particular features and/or combinations of components, other embodiments are possible having a combination of any features and/or components from any of embodiments described herein. The specific configurations of the various components can also be varied. For example, the size and specific shape of the various components can be different from the embodiments shown, while still providing the functions as described herein. By way of example, while the trays 120 are shown and described as having the specific contours 123 and/or 133, in other embodiments, a tray can have and/or can form any suitable contour configured to selectively engage or contact a portion of a biodiffusion chamber to at least temporarily maintain the biodiffusion chamber in a predetermined and/or desired position and/or orientation that can allow a user to access the injection port of the biodiffusion chamber. In some implementations, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

Any of the devices, components, and/or embodiments described herein can be packaged independently or packaged together as a kit including any suitable combination of the devices, components, and/or embodiments. For example, in some implementations, the chamber container 110 can be packaged independent of the tool container(s) 150. In other implementations, the chamber container 110 and a set of tool containers 150 can be packaged together as a kit. In some implementations, such a kit can include, for example, the chamber container 110, any number of trays 120, any number of biodiffusion chambers 10 disposed in the trays 120, any number of tool containers 150, any number of tools 170 disposed within the tool containers 150, and any number of seal members 175 coupled the tools 170. In other implementations, the kit need not include the seal members (e.g., the seal members can be packaged separately from the kit).

All of the products, compositions, and/or methods disclosed and/or claimed herein can be made and executed without undue experimentation in light of the present disclosure. While the products, compositions, and/or methods of this disclosure have been described in terms of specific embodiments, it will be apparent to those of skill in the art that variations and modifications may be applied to the products, compositions, and/or methods and in the steps or in the sequence of steps of the methods described herein without departing from the concept, spirit and scope of the disclosure. All such similar variations and modifications apparent to those skilled in the art are deemed to be within the spirit, scope, and concept of the disclosure.

What is claimed is:

1. An apparatus comprising one or more biodiffusion chambers, wherein the apparatus comprises:

a chamber container having a first portion and a second portion removably coupled to the first portion, the first portion and the second portion collectively defining an inner volume; and a tray configured to be removably disposed within the inner volume of the chamber container, the tray including a first portion and a second portion coupled to the first portion via a hinge, the first portion including a first retention surface, the second portion including a second retention surface, the tray configured to receive the one or more biodiffusion chambers between the first portion and the second portion such that each of the first retention surface and the second retention surface engage a portion of the one or more biodiffusion chambers to (1) place the one or more biodiffusion chambers in a predetermined orientation and (2) maintain the one or more biodiffusion chambers in a substantially fixed position relative to the tray, wherein the first portion of the tray includes a chamber region comprising a contour wherein the contour defines a seat configured to receive a portion of the one or more biodiffusion chambers, wherein the first retention surface is configured to be in contact with a first portion of a flange of the one or more biodiffusion chambers and the second retention surface is configured to be in contact with a second portion of the flange;

wherein the second portion of the flange is substantially opposite the first portion of the flange, wherein the apparatus is configured to at least temporarily store the one or more biodiffusion chambers.

2. The apparatus of claim 1, wherein the first retention surface and the second retention surface are configured to limit rotation of the biodiffusion chamber relative to the tray.

3. The apparatus of claim 1, wherein the second portion is configured to pivot about an axis defined by the hinge and relative to the first portion to transition the tray from a closed configuration to an open configuration.

4. The apparatus of claim 3, wherein first retention surface is configured to engage the portion of the biodiffusion chamber when tray is in the open configuration to maintain the biodiffusion chamber in the predetermined orientation.

5. The apparatus of claim 4, wherein the biodiffusion chamber includes an injection port, the injection port being accessible when the biodiffusion chamber is in the predetermined orientation.

6. The apparatus of claim 1, wherein the first retention surface is from a plurality of first retention surfaces, the second retention surface is from a plurality of second retention surfaces, and the biodiffusion chamber is from a plurality of biodiffusion chambers, the tray configured to receive the plurality of biodiffusion chambers between the first portion and the second portion such that each first retention surface from the plurality of first retention surfaces and each second retention surface from the plurality of second retention surfaces engage a portion of one biodiffusion chamber from the plurality of biodiffusion chambers.

7. The apparatus of claim 6, wherein the first portion includes a chamber region configured to receive the plurality of biodiffusion chambers, the chamber region of the first portion having a contour forming the plurality of first retention surfaces.

8. The apparatus of claim 7, wherein the contour of the chamber region forms a plurality of seats, each seat from the plurality of seats configured to receive a portion of a biodiffusion chamber from the plurality of biodiffusion chambers.

9. The apparatus of claim 8, wherein the second portion includes a chamber region configured to receive the plurality of biodiffusion chambers, the chamber region of the second portion having a contour forming the plurality of second retention surfaces.

10. The apparatus of claim 1, wherein the tray is a first tray, the apparatus further comprising:

a second tray configured to be removably disposed within the inner volume of the chamber container, the second tray including a first portion and a second portion coupled to the first portion via a hinge, the first portion of the second tray including a first retention surface, the second portion of the second tray including a second retention surface, the second tray configured to receive a biodiffusion chamber between the first portion and the second portion such that each of the first retention surface and the second retention surface of the second tray engage a portion of the biodiffusion chamber to maintain the biodiffusion chamber in a substantially fixed position relative to the second tray.

11. The apparatus of claim 1, further comprising a tool and a tool container, wherein the tool is configured to be used with the one or more biodiffusion chambers, wherein the tool container has a first portion and a second portion removably coupled to the first portion, wherein the first portion includes a tool region configured to receive the tool.

12. The apparatus of claim 11, further comprising a seal member, wherein the seal member is configured to be inserted into an injection port of the one or more biodiffusion chambers, and wherein the seal member is coupled to the tool.

13. The apparatus of claim 11, wherein the tool container is configured to at least temporarily couple to the chamber container in a stacked configuration.

14. A method of fixating one or more biodiffusion chambers, wherein the method comprises placing the one or more biodiffusion chambers into the apparatus of claim 1.

15. A method of fixating one or more biodiffusion chambers, wherein the method comprises placing the one or more biodiffusion chambers into the apparatus of claim 11.

16. A method of at least temporarily storing one or more biodiffusion chambers, wherein the method comprises placing the one or more biodiffusion chambers into the apparatus of claim 1.

17. A method of at least temporarily storing one or more biodiffusion chambers, wherein the method comprises placing the one or more biodiffusion chambers into the apparatus of claim 11.

* * * * *